(12) United States Patent
Joplin

(10) Patent No.: US 9,697,335 B2
(45) Date of Patent: Jul. 4, 2017

(54) METHODS AND SYSTEMS FOR AUTOMATED PHARMACEUTICAL DISPENSING

(71) Applicant: EXPRESS SCRIPTS, INC., St. Louis, MO (US)

(72) Inventor: Jonathan W. Joplin, Chesterfield, MO (US)

(73) Assignee: EXPRESS SCRIPTS, INC., St. Louis, MO (US)

(*) Notice: Subject to any disclaimer, the term of this patent is extended or adjusted under 35 U.S.C. 154(b) by 0 days.

(21) Appl. No.: 14/807,596

(22) Filed: Jul. 23, 2015

(65) Prior Publication Data

US 2017/0024541 A1  Jan. 26, 2017

(51) Int. Cl.
*G06F 19/00* (2011.01)
*G07F 17/00* (2006.01)

(52) U.S. Cl.
CPC ...... *G06F 19/3462* (2013.01); *G06F 19/3456* (2013.01); *G07F 17/0092* (2013.01)

(58) Field of Classification Search
CPC .............................. G07F 17/0092; B65B 5/103
See application file for complete search history.

(56) References Cited

U.S. PATENT DOCUMENTS

| | | | | |
|---|---|---|---|---|
| 3,871,156 A * | 3/1975 | Koenig | ................... | B65B 37/04 221/113 |
| 5,660,305 A * | 8/1997 | Lasher | .................. | A61J 7/0084 221/124 |
| 5,720,154 A * | 2/1998 | Lasher | ..................... | G07F 5/18 53/168 |
| 5,771,657 A | 6/1998 | Lasher et al. | | |
| 6,769,228 B1 | 8/2004 | Mahar | | |
| 6,892,512 B2 | 5/2005 | Rice et al. | | |
| 7,303,094 B2 * | 12/2007 | Hutchinson | ............. | B65B 5/103 221/197 |
| 7,624,894 B2 * | 12/2009 | Gerold | ................ | G07F 17/0092 221/123 |
| 7,631,670 B2 * | 12/2009 | Geltser | ................... | B65B 57/20 141/1 |
| 7,735,302 B2 * | 6/2010 | Monti | ..................... | B65B 5/103 53/247 |
| 7,765,776 B1 | 8/2010 | Leu et al. | | |
| 8,141,330 B2 * | 3/2012 | Henkel | ................... | B65B 5/103 53/237 |
| 8,172,112 B2 * | 5/2012 | Karwacki, Jr. | ......... | G07F 11/44 221/200 |
| 8,731,711 B1 | 5/2014 | Joplin et al. | | |
| 2006/0163271 A1 * | 7/2006 | Hatsuno | .................. | B65B 5/103 221/112 |

* cited by examiner

*Primary Examiner* — Timothy Waggoner
(74) *Attorney, Agent, or Firm* — Bryan Cave LLP

(57) ABSTRACT

A pharmaceutical order filling system receives pharmaceutical orders and uses an automated dispensing device to dispense pharmaceuticals into containers. The automated dispensing device is configured with a filling cabinet that stores and dispenses measured quantities of pharmaceuticals and is further configured to stage measured quantities of pharmaceuticals in buffer tubes to enable efficient fulfillment of the pharmaceutical orders. Containers may be disposed on a pallet which may be moved within an automated dispensing device to place the containers under buffer tubes to receive measured quantities of pharmaceuticals from the buffer tubes into appropriate containers in an efficient manner.

23 Claims, 14 Drawing Sheets

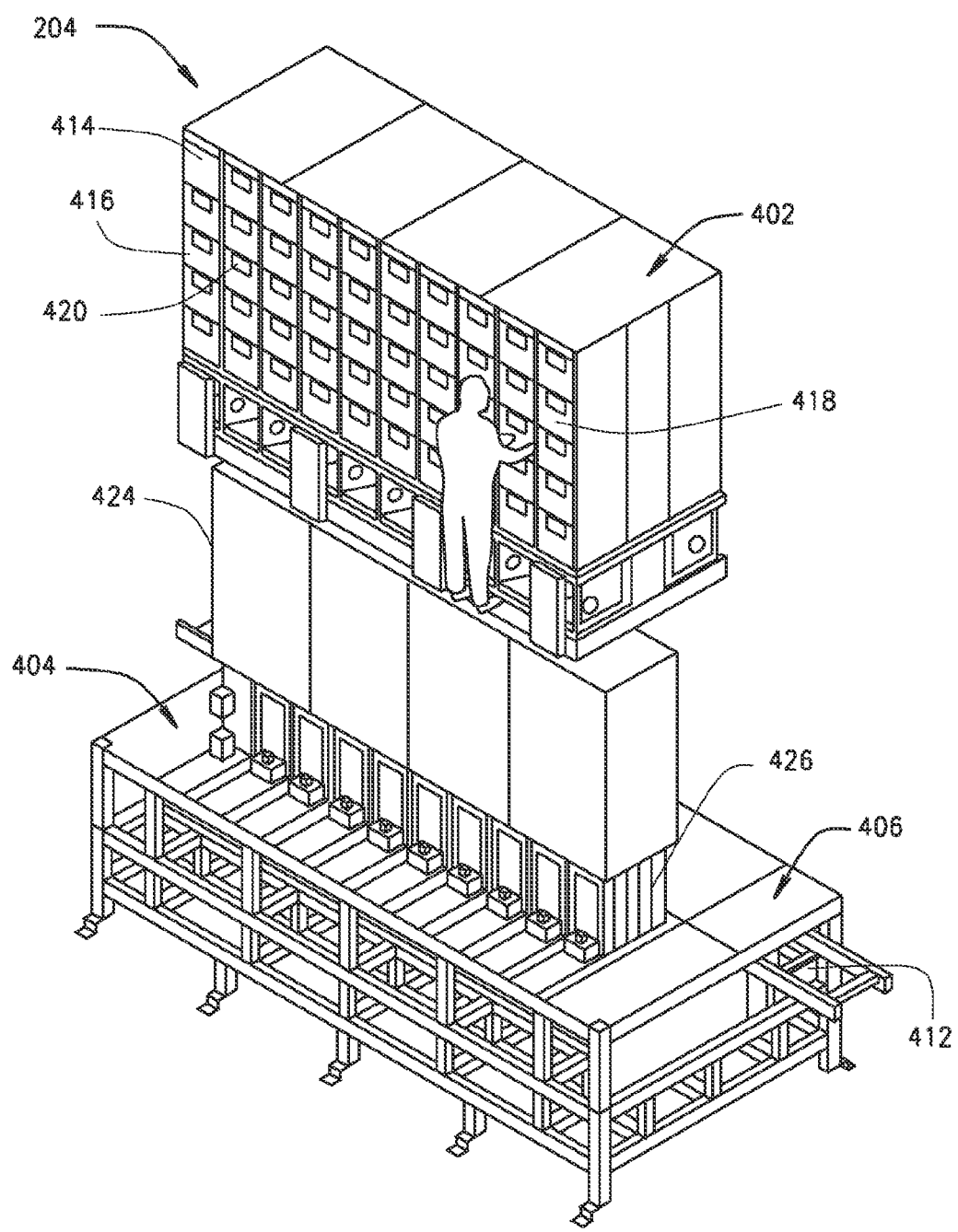
F I G . 4

METHODS AND SYSTEMS FOR AUTOMATED PHARMACEUTICAL DISPENSING

FIELD

The present application relates generally to the technical field of automated filling centers. In a specific example, the present application may relate to a high volume fulfillment center, e.g., a high volume pharmacy and to systems and devices used in filling prescriptions and prescription orders at a high volume pharmacy.

BACKGROUND

A high-volume pharmacy may process and fill a large number of prescriptions and prescription orders. Automated systems may be used by a high volume pharmacy to process and fulfill prescriptions.

Frequently, more than one prescription drug is required to complete a prescription order. Portions of the prescription order may be fulfilled in different areas of the high-volume pharmacy. After fulfillment, the fulfilled prescriptions may be gathered into a complete prescription order for shipping.

BRIEF DESCRIPTION OF THE DRAWINGS

FIG. 4 is a perspective view of an automated dispensing subsystem that may be deployed within the automated dispensing device of FIG. 2, according to an example embodiment;

DETAILED DESCRIPTION

Example systems and methods for automated pharmaceutical dispensing are described. In the following description, for purposes of explanation, numerous specific details are set forth in order to provide a thorough understanding of example embodiments. It will be evident, however, to one of ordinary skill in the art that these embodiments may be practiced without these specific details.

Generally, a prescription order is generated for a high volume pharmacy. The prescription order may include more than one prescription drug for fulfillment. Each prescription drug in a prescription order is an order component of the prescription order. Generally, the order components are pill bottles or other containers and packaging having a measured quantity of a prescription drug therein. These containers may be filled by a mostly manual process, through a semiautomatic process, or a more fully automated process. Various factors may affect the availability of filling drugs through these processes in a pharmacy. A more fully automated process may be employed in a mail order pharmacy to fill containers with most frequently used drugs.

Figure 1:
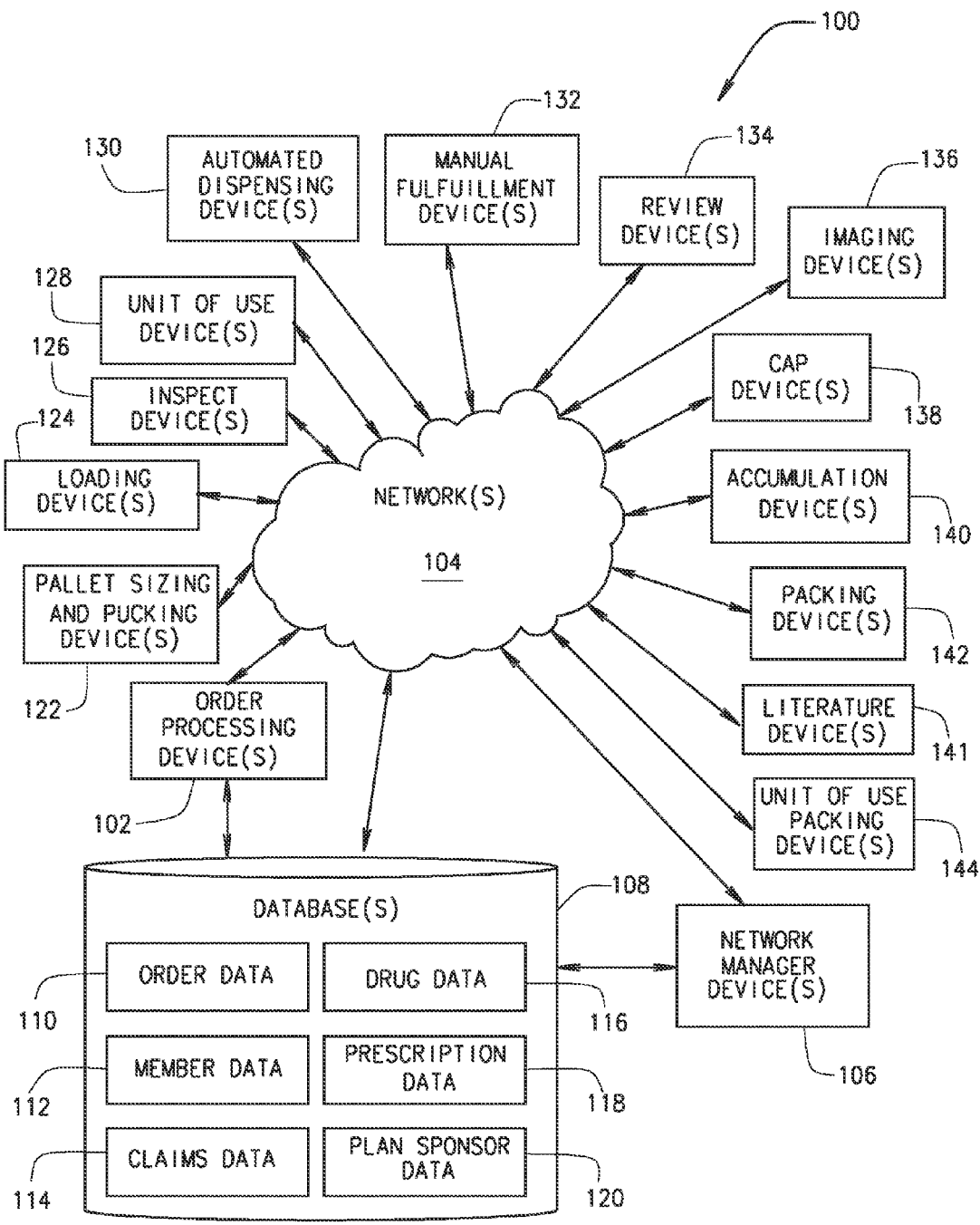
FIG. 1 is a block diagram of an example system, according to an example embodiment.

FIG. 1 is a block diagram of an example system 100, according to an example embodiment. While the system 100 is generally described as being deployed in a high volume pharmacy (e.g., a mail order pharmacy, a direct delivery pharmacy, an automated pharmacy, and the like), the system 100 may otherwise be deployed. The system 100 may include an order processing device 102 in communication with a benefit manager device 106 over a network 104. In an example embodiment, the order processing device 102 may implement functions described in U.S. patent application Ser. No. 12/874,107, which is hereby incorporated by reference, to move a patient to a high volume pharmacy. Additional devices which may be in communication with the benefit manager device 106 and/or the order processing device 102 over network 104 include: database(s) 108 which may store one or more than one of order data 110, member data 112, claims data 114, drug data 116, prescription data 118, and plan sponsor data 120; pallet sizing and pucking device(s) 122; loading device(s) 124; inspect device(s) 126; unit of use device(s) 128; automated dispensing device(s) 130; manual fulfillment device(s) 132; review device(s) 134; imaging device(s) 136; cap device(s) 138; accumulation device(s) 140; literature device(s) 141; packing device(s) 142; and unit of use packing device(s) 144. The system 100 may also include additional devices, which may communicate with each other over network 104 or directly.

The order processing device 102 may receive information about prescriptions being filled at a pharmacy in which the order processing device 102 is deployed. In general, the order processing device 102 is a device located within or otherwise associated with a pharmacy location to enable fulfillment of a prescription by dispensing prescription drugs. In some embodiments, the order processing device 102 may be a device separate from a pharmacy that enables communication with other devices located within a pharmacy. For example, the order processing device 102 may be in communication with another order processing device 102 and/or other devices 122-144 located with a pharmacy. In some embodiments, an external pharmacy order processing device 102 may have limited functionality (e.g., as operated by a patient requesting fulfillment of a prescription drug) when an internal pharmacy order processing device 102 may have greater functionality (e.g., as operated by a pharmacy).

The order processing device 102 may track a prescription order as it is fulfilled. A prescription order may include one or more than one prescription to be filled by the pharmacy. The order processing device 102 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 102 may operate on its own or in combination with the benefit manager device 106. The order processing device 102 may track and/or schedule the literature or other paperwork associated with each order or multiple prescription orders that are being shipped together.

Examples of the devices 102, 106 include a set-top box (STB), a receiver card, a mobile telephone, a personal digital assistant (PDA), a display device, a portable gaming unit, a tablet, and a computing system; however other devices may also be used. For example the devices 102, 106 may include a mobile electronic device, such an IPHONE or IPAD device by Apple, Inc. mobile electronic devices powered by ANDROID by Google, Inc. and a BLACKBERRY device by Blackberry Limited. The devices 102, 106 may also include other computing devices, such as desktop computing devices, notebook computing devices, netbook computing devices, gaming devices, and the like. The devices 102, 106 may include a processor, a memory to store data and instructions, and communication functionality. Other types of electronic devices that can use rules and instructions to execute various functions may also be used.

Examples of the network 104 include Mobile Communications (GSM) network, a code division multiple access (CDMA) network, $3^{rd}$ Generation Partnership Project (3GPP), an Internet Protocol (IP) network, a Wireless Application Protocol (WAP) network, a WiFi network, or an IEEE 802.11 standards network, as well as various combinations thereof. The network 104 may include optical communications. The network 104 may be a local area network or a global communication network, such as the Internet. Other conventional and/or later developed wired and wireless networks may also be used. In some embodiments, the network 104 may include a prescribing network such as the electronic prescribing network operated by Surescripts of Arlington, Va.

The benefit manager device 106 is a device operated by an entity at least partially responsible for creation and/or management of the pharmacy or drug benefit. While this benefit manager operating the benefit manager device 106 is typically a pharmacy benefit manager (PBM), other entities may operate the benefit manager device 106 either on behalf of themselves, the PBM, or another entity. For example, the benefit manager may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmacies may be retail pharmacies, mail order pharmacies, or otherwise.

Some of the operations of the PBM that operates the benefit manager device 106 may include the following. A member (or a person on behalf of the member) of a pharmacy benefit plan administered by or through the PBM attempts to obtain a prescription drug at a retail pharmacy location where the member can obtain drugs in a physical store from a pharmacist or pharmacist technician, or in some instances through mail order drug delivery from a mail order pharmacy location. The member may also obtain a prescription drug directly or indirectly through the use of a machine, such as a kiosk, vending unit, mobile electronic device, or a different type of mechanical, electrical, electronic communication device and/or computing device.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of a plan sponsor or client with the PBM. The member's co-pay may be based on a flat co-pay (e.g., $10), co-insurance (e.g., 10%), and/or a deductible (e.g., for first $500 of annual prescription drug spend) for certain prescription drugs, certain types and/or classes of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug. The co-pay may also vary based on the delivery channel used to receive the prescription drug. For example, the co-pay for receiving prescription drug from a mail order pharmacy location may be less than the co-pay for receiving prescription drug from a retail pharmacy location.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing an applicable formulary of the member to determine appropriate co-pay, coinsurance, and deductible for the prescription drug, and performing a drug utilization review (DUR) on the member. The PBM then provides a response to the pharmacy following performance of at least some of the aforementioned operations. As part of the adjudication, the plan sponsor (or the PBM on behalf of the plan sponsor) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be based at least in part on the type of pharmacy network in which the pharmacy is included. Other factors may be used to determine the amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher. Some or all of the foregoing operations may be performed by executing instructions on the benefit manager device 106 and/or an additional device.

In some embodiments, at least some of the functionality of the order processing device 102 may be included in the benefit manager device 106. The order processing device 102 may be in a client-server relationship with the benefit manager device 106, a peer-to-peer relationship with the benefit manager device 106, or in a different type of relationship with the benefit manager device 106.

The order processing device 102 and/or the benefit manager device 106 may be in communication directly (e.g., through local storage or peer-to-peer connection(s)) and/or through the network 104 (e.g., in a cloud configuration or software-as-a-service) with a database 108 (e.g., as may be retained in memory or otherwise). The database 108 may be deployed on the order processing device 102, the benefit manager device 106, on another device of the system 100, or otherwise. The database 108 may store order data 110, member data 112, claims data 114, drug data 116, prescription data 118, and/or plan sponsor data 120. Other data may be stored in the database 108.

The order data 110 may include data related to the order of prescriptions including the type (e.g., drug name and strength) and quantity of each prescription in a prescription order. The order data 110 may also include data used for completion of the prescription, such as prescription materials and/or the type and/or size of container in which the drug is or is preferably dispensed. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 110 may be used by a high volume fulfillment center to fulfill a pharmacy order. In some embodiments, the order data 110 includes verification information associated with fulfillment of the prescription in the pharmacy. For example, the order data 110 may include videos and/or images taken of (i) the prescription drug prior to dispensing, during dispensing, and/or after dispensing, (ii) the prescription container (e.g., a prescription bottle and sealing lid) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other type of verification information such as bar code data read from pallets used to transport prescriptions within the pharmacy may also be stored as order data 110.

The member data 112 includes information regarding the members associated with the benefit manager. The information stored as member data 112 may include personal information, personal health information, protected health information, and the like. Examples of the member data 112 include name, address, telephone number, e-mail address, prescription drug history, and the like. The member data 112 may include a plan sponsor identifier that identifies the plan sponsor associated with the member and/or a member identifier that identifies the member to the plan sponsor. The member data 112 may include a member identifier that identifies the plan sponsor associated with the patient and/or a patient identifier that identifies the patient to the plan sponsor. The member data 112 may also include, by way of example, dispensation preferences such as type of label, type of cap, message preferences, language preferences, or the like. The member data 112 may be accessed by various devices in the pharmacy, e.g., the high volume fulfillment center, to obtain information utilized for fulfillment and shipping of prescription orders. In some embodiments, an external order processing device 102 operated by or on behalf of a member may have access to at least a portion of the member data 112 for review, verification, or other purposes.

In some embodiments, the member data 112 may include information for persons who are patients of the pharmacy but are not members in a benefit plan being provided by the benefit manager. For example, these patients may obtain drug directly from the pharmacy, through a private label service offered by the pharmacy, the high volume fulfillment center, or otherwise. In general, the use of the terms member and patient may be used interchangeably herein.

The claims data 114 includes information regarding pharmacy claims adjudicated by the PBM under a drug benefit program provided by the PBM for one, or more than one, plan sponsors. In general, the claims data 114 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included. In some embodiments, other types of claims beyond prescription drug claims may be stored in the claims data 114. For example, medical claims, dental claims, wellness claims, or other type of health care-related claims for members may be stored as a portion of the claims data 114.

In some embodiments, the claims data 114 includes claims that identify the members with whom the claims are associated. In some embodiments, the claims data 114 includes claims that have been de-identified (e.g., associated with a unique identifier but not with a particular, identifiable member).

The drug data 116 may include drug name (e.g., technical name and/or common name), other names by which the drug is known by, active ingredients, an image of the drug (e.g., in pill form), and the like. The drug data 116 may include information associated with a single medication or multiple medications.

The prescription data 118 may include information regarding prescriptions that may be issued by prescribers on behalf of patients, who may be members of the drug benefit plan, for example to be filled by a pharmacy. Examples of the prescription data 118 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 110 may be linked to associated member data, claims data 114, drug data 116, and/or prescription data 118.

The plan sponsor data 120 includes information regarding the plan sponsors of the benefit manager. Examples of the plan sponsor data 120 include company name, company address, contact name, contact telephone number, contact e-mail address, and the like.

The order processing device 102 may direct at least some of the operations of the devices 122-144, recited above. In some embodiments, operations performed by one of these devices 122-144 may be performed sequentially, or in parallel with the operations of another device as may be coordinated by the order processing device 102. In some embodiments, the order processing device 102 tracks a prescription with the pharmacy based on operations performed by one or more of the devices 122-144.

In some embodiments, the system 100 may transport prescription drug containers (e.g., between one or more than one of the devices 122-144 in the high volume fulfillment center) by use of pallets. The pallet sizing and pucking device 122 may configure pucks in a pallet. A pallet may be a transport structure for a number of prescription containers, and may include a number of cavities. A puck may be placed in one or more than one of the cavities in a pallet by the pallet sizing and pucking device 122. A puck may include a receptacle sized and shaped to receive a prescription container. Such containers may be supported by the pucks during carriage in the pallet and during movement through the fulfillment process. Different pucks may have differently sized and shaped receptacles to accommodate containers of differing sizes, as may be appropriate for different prescriptions. Pucks allow the standardization of equipment engaging differently sized drug containers such that some automated equipment can move the drug container by gripping the puck that is supporting the container and allow the use of a standardized pallet that holds a plurality of pucks have a same outer dimension while having differently sized receptacles therein to hold differently sized drug containers. The pucks may also operate to ensure that a drug container is centered in a location on the pallet.

The arrangement of pucks in a pallet may be determined by the order processing device 102 based on prescriptions which the order processing device 102 decides to launch. In general, prescription orders in the order database 110 reside in one or more than one queues, and are generally launched in a first-in-first-out order. However, the order processing device 102 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implemented directly in the pallet sizing and pucking device 122, in the order processing device 102, in both devices 102, 122, or otherwise. Once a prescription is set to be launched, a puck suitable for the appropriate size of container for that prescription may be positioned in a pallet by a robotic arm or pickers. The pallet sizing and pucking device 122 may launch a pallet once pucks have been configured in the pallet. The loading device 124 may load prescription containers into the pucks on a pallet by a robotic arm, pick and place mechanism, or the like. In one embodiment, the loading device 108 has robotic arms or pickers to grasp a prescription container and move it to and from a pallet. The loading device 124 may also print a label which is appropriate for a container that is to be loaded onto the pallet, and apply the label to the container. The pallet may be located on a conveyor assembly during these operations. In an example embodiment, the drug containers may be positioned in the pucks by the loading device 124 prior to the pucks being placed in the pallet. The inspect device 126 may verify that containers in a pallet are correctly labeled and in the correct spot on the pallet. The inspect device 126 may scan the label on one or more than one container on the pallet. Labels of containers may be scanned or imaged in full or in part by the inspect device 126. Such imaging may occur after the container has been lifted out of its puck by a robotic arm, picker, or the like, or may be otherwise scanned or imaged while retained in the puck. In some embodiments, images and/or video captured by the inspect device 126 may be stored in the database 108 as order data 110.

The unit of use device 128 may temporarily store, monitor, label and/or dispense unit of use products. In general, unit of use products are prescription drug products that may be delivered to a patient or member without being repackaged at the pharmacy. These products may include pills in container, pills in a blister pack, inhalers, and the like. Pills to be placed in a container may include, and not be limited to, capsules, tablets, caplets, lozenges, and other solid medium with a pharmaceutical component that may be ingested by a person or other mammal. Prescription drug products dispensed by the unit of use device 128 may be packaged individually or collectively for shipping, or may be shipped in combination with other prescription drugs dispensed by other devices in the high volume fulfillment center.

The automated dispensing device 130 may include one or more than one devices that dispense prescription drugs or pharmaceuticals into prescription containers in accordance with one or multiple prescription orders. In general, the automated dispensing device 130 may include mechanical and electronic components with, in some embodiments, software and/or logic to facilitate pharmaceutical dispensing that would otherwise be performed in a manual fashion by a pharmacist and/or pharmacist technician. For example, the automated dispensing device 130 may include high volume fillers that fill a number of prescription drug types at a rapid rate and blister pack machines that dispense and pack drugs into a blister pack or other pre-packaged form of pills. Prescription drugs dispensed by the automated dispensing devices 130 may be packaged individually or collectively for shipping, or may be shipped in combination with other prescription drugs dispenses by other devices in the high volume fulfillment center.

The automated dispensing device 130 may be used, for example, to dispense commonly prescribed dispense drugs in an automatic or semiautomatic method into containers. Drugs may be dispensed in connection with filling one or more than one prescriptions (or portions of prescriptions). Drugs dispensed by the automated dispensing device 130 may be tablets, pills, capsules, caplets, or other types of drugs suitable for dispensing by a the automated dispensing device 130.

The manual fulfillment device 132 may provide for manual fulfillment of prescriptions. For example, the manual fulfillment device 132 may receive or obtain a container and enable fulfillment of the container by a pharmacist or pharmacy technician. In some embodiments, the manual fulfillment device 132 provides the filled container to another device in the system 100. In an example embodiment, the container may be joined with other containers in a prescription order for a patient or member, e.g., on a pallet or at the accumulation device 140. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter). Prescription drugs dispensed by the manual fulfillment device 132 may be packaged individually or collectively for shipping, or may be shipped in combination with other prescription drugs dispenses by other devices in the high volume fulfillment center.

The review device 134 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 134 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review can be performed at the manual station.

The imaging device 136 may image containers after they have been filled with pharmaceuticals. The imaging device 136 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 102, and/or stored in the database 110 as part of the order data 110.

The cap device 138 may be used to cap or otherwise seal a prescription container. In some embodiments, the cap device 138 may secure a prescription container with a type of cap in accordance with a patient preference (e.g., a preference regarding child resistance), a plan sponsor preference, a prescriber preference, or the like. The cap device 138 may also etch a message into the cap or otherwise associate a message into the cap, although this process may be performed by a subsequent device in the high volume fulfillment center. Etching may be performed according to the teachings in U.S. patent application Ser. No. 14/313,042, which is hereby incorporated by reference. The accumulation device 140 accumulates various containers of prescription drugs in a prescription order. The accumulation device 140 may accumulate prescription containers from various devices or areas of the pharmacy. For example, the accumulation device 140 may accumulate prescription containers from the unit of use device 128, the automated dispensing device 130, the manual fulfillment device 132, and the review device 134, at the high volume fulfillment center. The accumulation device 140 may be used to group the prescription containers prior to shipment to the member or otherwise. In some embodiments, the literature device 141 folds or otherwise prepares the literature for inclusion with a prescription drug order (e.g., in a shipping container). In some embodiments, the literature device 141 that prints the literature may be separate from the literature device that prepares the literature for inclusion with a prescription order.

The packing device 142 packages a prescription order in preparation for shipping the order. The packing device 142 may box, bag, or otherwise package the fulfilled prescription order for delivery. The packing device 142 may further place inserts, e.g., literature or other papers into the packaging received from the literature device 141 or otherwise. For example, bulk prescription orders may be shipped in a box, while other prescription orders may be shipped in a bag which may be a wrap seal bag. The packing device 142 may label the box or bag with the address and a recipient's name. The label may be printed and affixed to the bag or box, be printed directly onto the bag or box, or otherwise associated with the bag or box. The packing device 142 may sort the box or bag for mailing in an efficient manner (e.g., sort by delivery address). The packing device 142 may include ice or temperature sensitive elements for prescriptions which are to be kept within a temperature range during shipping in order to retain efficacy or otherwise. The ultimate package may then be shipped through postal mail, through a mail order delivery service that ships via group and/or air (e.g., UPS, FEDEX, or DHL), through delivery service, through a local delivery service (e.g., a courier service), through a locker box at a shipping site (e.g., an AMAZON locker or a post office box), or otherwise.

The unit of use packing device 144 packages a unit of use prescription order in preparation for shipping the order. The unit of use packing device 144 may include manual scanning of containers to be bagged for shipping to verify each container in the order. In an example embodiment, the manual scanning may be performed at a manual station.

While the system 100 in FIG. 1 is shown to include single devices 102, 106, 122-144 multiple devices may be used. The devices 102, 106, 122-144 may be the same type or model of device or may be different device types or models. When multiple devices are present, the multiple devices may be of the same device type or models or may be a different device type or model. The types of devices 102, 106, 122-144 shown in FIG. 1 are example devices. In other configurations of the system 100, lesser, additional, or different types of devices may be included.

Moreover, the system 100 shows a single network 104; however, multiple networks can be used. The multiple networks may communicate in series with each other to link the devices 102, 106, 122-144 or in parallel to link the devices 102, 106, 122-144. Multiple devices may share processing and/or memory resources. The devices 102, 106, 122-144 may be located in the same area or in different locations. For example, the devices 102, 106, 122-144 may be located in a building or set of adjoining buildings. The devices 102, 106, 122-144 may be interconnected (e.g. by conveyors), networked, and/or otherwise in contact with one another or integrated with one another e.g., at the high volume fulfillment center. In addition, the functionality of a device may be split among a number of discrete devices and/or combined with other devices.

The system 100 may include a single database, or multiple databases, maintained by respective devices operated by or on behalf one or a number of different persons and/or organizations. The communication may occur directly (e.g., through local storage) and/or through the network 104 (e.g., in a cloud configuration or software-as-a-service) with a device that stores a respective database.

Figure 2:
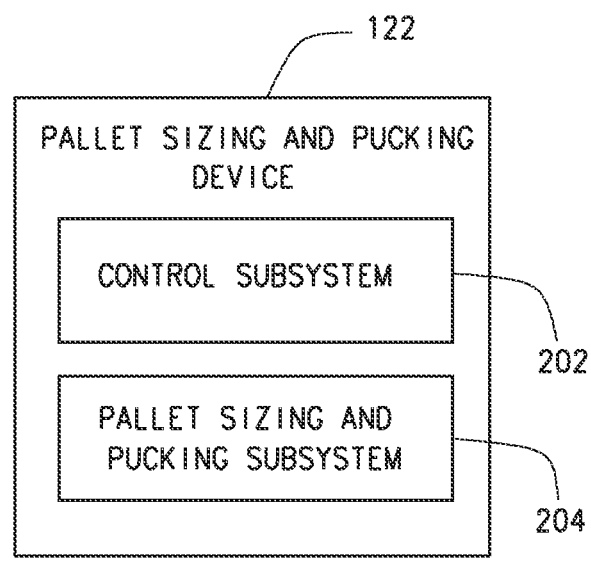
FIG. 2 is a block diagram of an example automated dispensing device that may be deployed within the system of FIG. 1, according to an example embodiment.

FIG. 2 illustrates an automated dispensing device 130, according to an example embodiment. The automated dispensing device 130 may be deployed in the system 100 of FIG. 1, or may otherwise be used. The automated dispensing device 130 may include a control subsystem 202 and an automated dispensing subsystem 204. The control subsystem 202 may include one or more module and enables the automated dispensing device 130 to control the automated dispensing subsystem 204, while the automated dispensing subsystem 204 may include one or more device and enables the automated dispensing device 130 with dispensing operations (e.g., dispensing a measured quantity pharmaceuticals into a container).

An example deployment of the automated dispensing device 130 is within the system 100. In such a deployment, the system 100 includes one or more than one conveyor or other devices to facilitate transporting containers or pallets of containers through mechanical devices within the system 100, such as devices to label, fill, cap, and check containers. The automated dispensing device 130 may be otherwise deployed.

Figure 3:
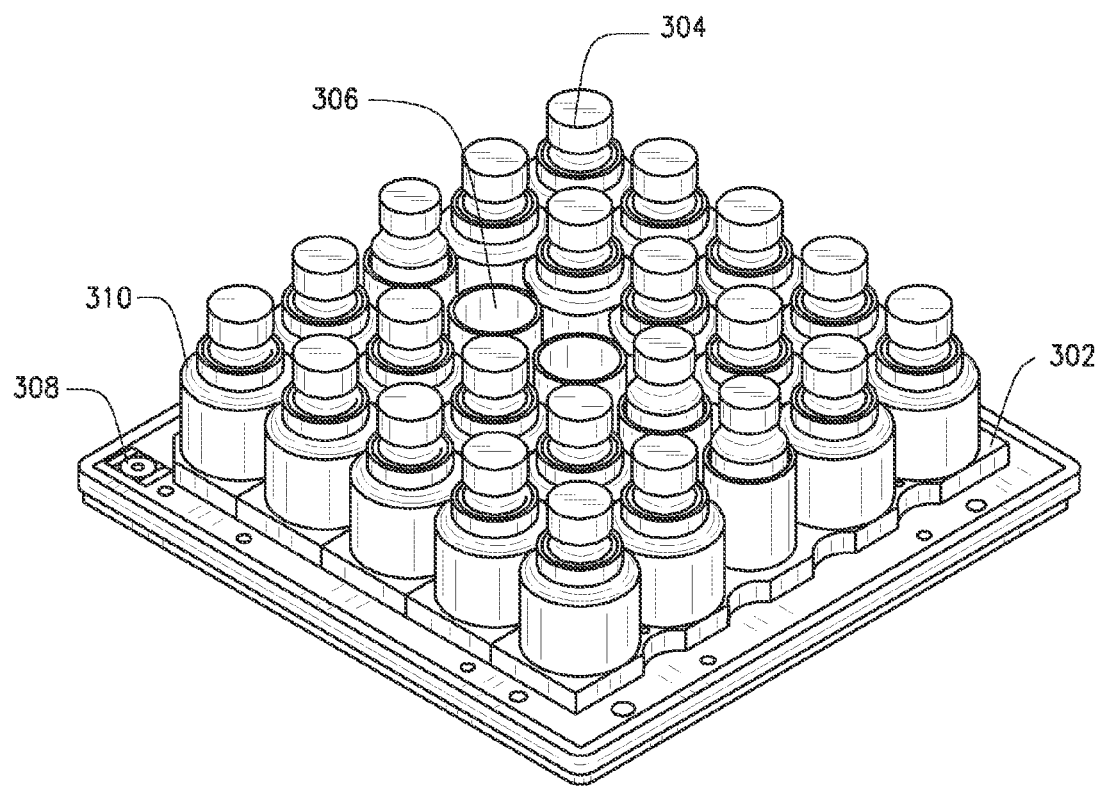
FIG. 3 is a top, perspective view of a pallet that may be deployed within the system of FIG. 1, according to an example embodiment.

FIG. 3 illustrates a pallet 302, according to an example embodiment. The pallet 302 may be used in the system 100 of FIG. 1 (e.g., by the automated dispensing device 130), or may be otherwise used.

The pallet 302 may be a transport structure for a number of prescription containers 304, and may include a number of cavities 306. While the pallet 302 is shown to include 25 cavities in a five by five cavity row/column configuration, other numbers of categories and/or cavity configurations of varying shapes, size, and/or dimensions may be used. In some embodiments the pallet may be substantially square and, in such an embodiment, have a width and length of between approximately 18 inches and 22 inches (e.g., approximately 18 inches, 19 inches, 20 inches, 21 inches, or 22 inches). In some embodiments, the width and/or length may be greater than approximately 22 inches or less than approximately 18 inches.

In an example embodiment, the cavities 306 are spaced on the pallet 302 such that the center point of adjacent cavities 306 is between approximately 3 inches and 4 inches (e.g., approximately 3 inches, 3.25 inches, 3.5 inches, 3.75 inches or 4 inches). In another example embodiment, the distance between center points of adjacent cavities 306 is more than approximately 4 inches. In yet another example embodiment, the center points of cavities 306 are less than approximately 3 inches apart.

The pallet 302 may be made in whole or in part of metal, such as aluminum. Other suitable materials may be used for the pallet 302, such as plastic. The pallet 302 may be rigid so that the cavities remain in a known location that can be tracked while the pallet moves through the system 100. The pallet 302 may include bumpers.

In some embodiments, other carriers beyond the pallet 302 and/or no carrier may be used to move containers or groups of containers through the system 100 or via the automated dispensing subsystem 204.

The pallet 302 may retain one or more than one containers 304. A container 304 is generally cylindrical and may be of one or a variety of sizes utilized by a pharmacy for fulfillment of a prescription. For example, a pharmacy may have two different sized containers or three different sized containers. Any number of different sized containers may be used with the pallet 302. While the container 304 is generally denoted as being used with the pallet 302, the containers 304 may otherwise be used in the system 100 or in a different system. Shapes beyond cylindrical shapes may be used for the containers 304. Examples of other shapes include regular prisms, elliptical cylinders, and combinations thereof. The receptacle of a puck may be sized to receive and support the outer shape of the container. The containers 304 may be disposed in the pallet 302 such that they are close to one another but do not touch.

The pallet 302 may include a radio-frequency identification (RFID) tag 308. The RFID tag 308 may be an active RFID tag, such as an active RFID tag with a close reading range. In some embodiments, the RFID tag 308 is an active, narrowband, read/write RFID tag.

The RFID tag 308 of a particular pallet 302 may store data (or otherwise facilitate the access of data, e.g., from the database 108) associated with the containers 304 that have been, are, and/or will be placed within the pallet 302, such as the order data 110, the member data 112, the claims data 114, the drug data 116, the prescription data 118, and/or the plan sponsor data 120 associated with such containers 304. Other data may be stored by and/or or associated with the RFID tag 314, such as the age of the pallet 302, the number of times the pallet 302 has been used to transport containers 304 through the system 100, the number of errors associated with the pallet 302, and the like. The RFID tag 314 may also store the position of individual containers on the pallet 302. In an example embodiment, the RFID tag 308 of the pallet 302, while deployed within an automated dispensing subsystem 204, stores data associated with one or more of the following data fields: (1) container identifiers, (2) identifier of the particular automated dispensing subsystem 204, (3) identifiers of the particular cells from which a particular container will be filled (as described below), (4) container properties (e.g., the status of containers 304 on the pallet 302, such as whether the containers 304 have passed an inspection station and have been identified as containers 304 to be filled in the particular automated dispensing subsystem 204), and (5) the pallet route within the automated dispensing subsystem 204.

The pucks 310 may be used to modify the size of the cavities 306 to allow the pallet 302 to accommodate different sizes of the containers 304.

Figure 5:
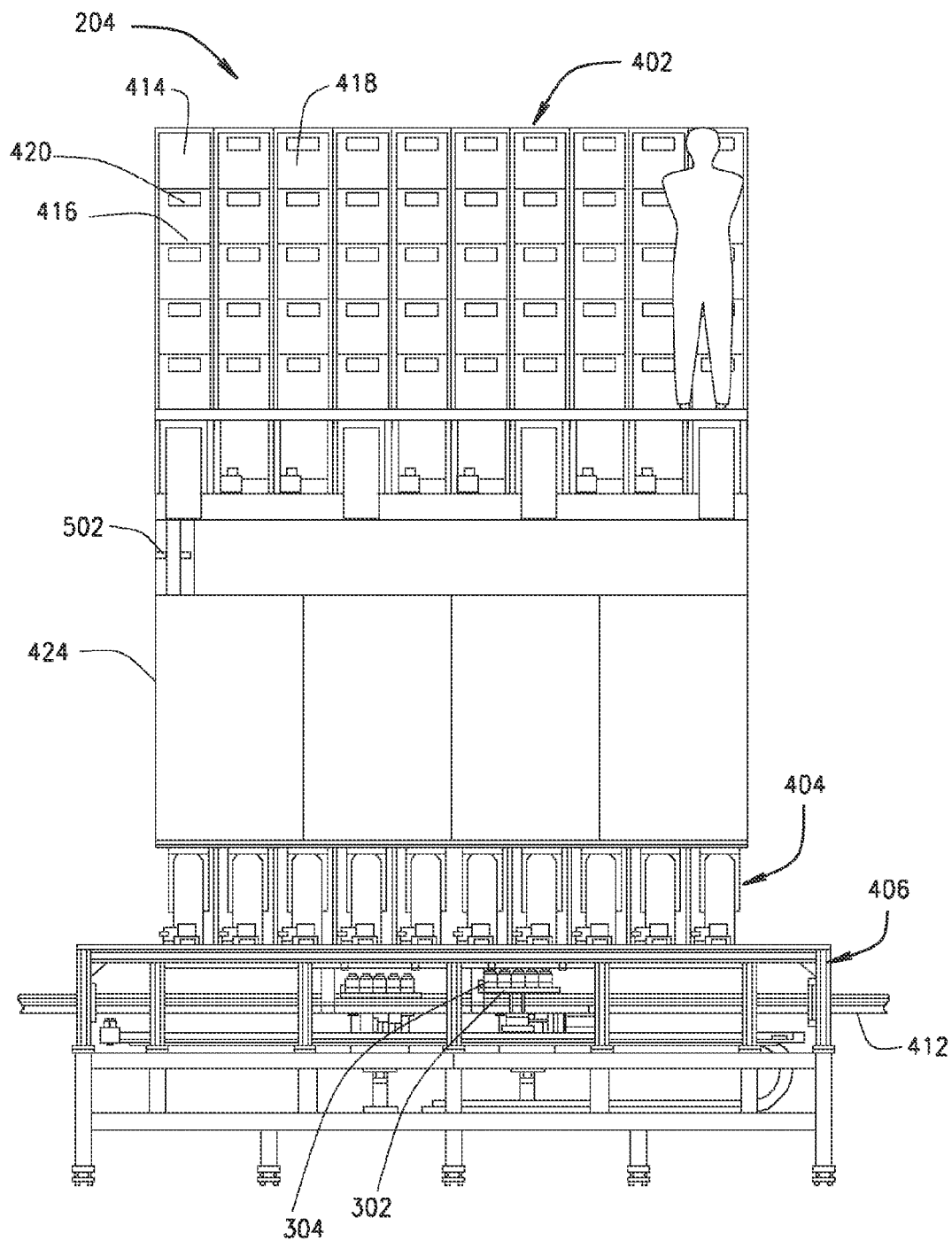
FIG. 5 is a front view of the automated dispensing subsystem of FIG. 4.
Figure 6:
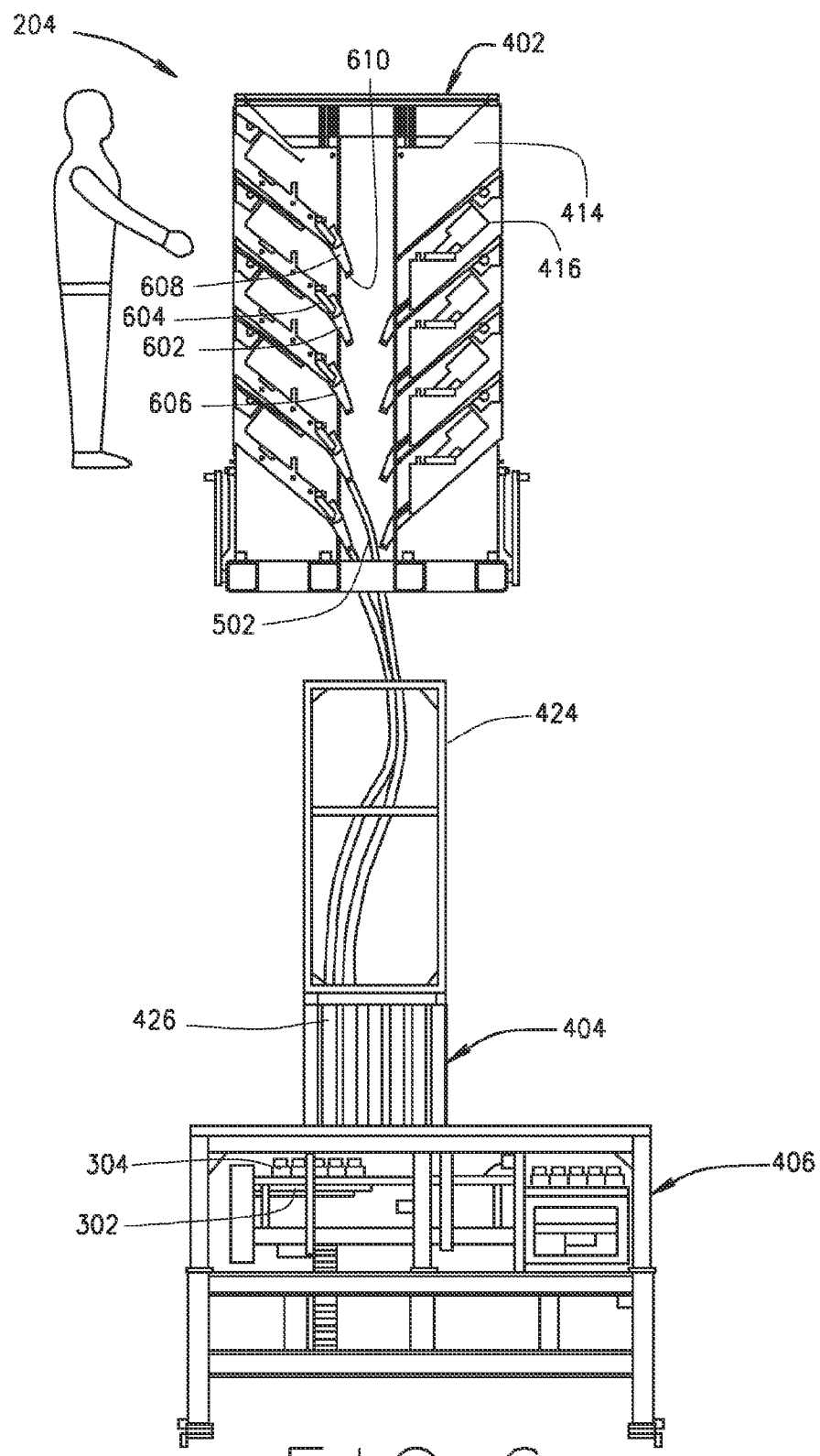
FIG. 6 is a side, cross-sectional view of the automated dispensing subsystem of FIG. 4.

FIGS. 4-6 illustrate the automated dispensing subsystem 204, according to an example embodiment. The automated dispensing subsystem 204 may be deployed within the automated dispensing device 130, or may otherwise be deployed. The automated dispensing subsystem 204 enables dispensing of a number of different types of pharmaceuticals in an automatic or semiautomatic manner.

The automated dispensing subsystem 204 includes a filling cabinet 402, a prefill assembly 404, and a pallet assembly 406. The filling cabinet 402 stores pharmaceuticals to be dispensed into containers via the prefill assembly 404 and dispenses measured quantities of pharmaceuticals into the prefill assembly 404. The prefill assembly 404 stores the measured quantities of pharmaceuticals and dispenses the measured quantities of pharmaceuticals received from the filling cabinet 402 into containers 304 on the pallet 302 while in the pallet assembly 406.

A pallet conveyor 412 may transport the pallets 302 through some or all of the devices within the system 100, such as the automated dispensing device 130. The pallet assembly 406 receives the pallets 302 via the pallet conveyor 412 and moves the pallets 302 within the pallet assembly 406 such that pharmaceuticals dispensed by the automated dispensing subsystem 204 are dispensed into the containers 304 on the pallet 302.

The pallet conveyor 412 may be a chain conveyor or a belt driven conveyor, e.g., a belted Bosch TS2 belt-driven conveyors; other types of conveyors may be used for the pallet conveyor 412, such as a chain conveyor. In some embodiments, the pallet conveyor 412 is a low friction, high speed conveyor.

Although pallets are generally described herein as employed to move a group of containers through the system 100 or within the automated dispensing subsystem 204, trays or other types of carriers may be employed to move a group of containers 304 through the system 100 or within the automated dispensing subsystem 204.

The filling cabinet 402 may be physically housed, located, positioned or installed above the prefill assembly 404 and the pallet assembly 406. For example, the filling cabinet 402 may be located on a first floor (e.g., in a building) and the prefill assembly 404 and the pallet assembly 406 may be located on a second floor (e.g., in the same building) below the filling cabinet 402. These components of the automated dispensing subsystem 204 may be otherwise positioned, e.g., in a position to utilize gravity to move pharmaceuticals from the filling cabinet 402 to the prefill assembly 404 and then to the containers on 304 the pallet 302. For example, some portion of the filling cabinet 402 may extend below the first floor.

The filling cabinet 402 may include multiple cells 414. The cells 414 may each be adapted to hold a different pharmaceutical. The cells 414 may be adapted to receive inserts 416. For example, the inserts 416 may be slidably inserted into the cells 414. The inserts 416 may be adapted to hold pharmaceuticals to be dispensed into the containers 304 via the automated dispensing subsystem 204. The cells 414 may receive pharmaceuticals, retain such pharmaceuticals, and dispense measured quantities of such pharmaceuticals into the prefill assembly 404. The insert 416 may be adapted to be removably received within the cell 414. For example, the insert 416 may pull out of the cell 414 like a drawer or a fixable pouch. In some embodiments, the cells 414 and the inserts 416 may be provided on opposite sides of the filling cabinet 402. Thus, the first and second sides of the filling cabinet 402 may be separately accessible. The filling cabinet 402 may include fifty cells 414 per side, so in an embodiment in which cells 414 are provided on opposite sides of the filling cabinet 402, the filling cabinet 402 may include up to and including 100 cells. In other embodiments, fewer or more than 50 cells may be included per side and/or fewer or more than 100 cells may be included per filling cabinet 402. Each cell 414 may receive an insert 416 filled (or to be filled) with a different pharmaceutical or multiple cells 414 may each receive an insert 416 filled (or to be filled) with the same pharmaceutical. For example, more than one insert 416 may be filled with a commonly prescribed pharmaceutical.

The insert 416 may include a face plate 418 with a door 420. The door 420 may be adapted to lock and to unlock to be opened. For example, the door 420 may be adapted to be locked unless and until it is unlocked. The door 420 may be adapted to unlock pursuant to a process that mitigates risk of unauthorized access to the pharmaceuticals within the insert 416 and/or to mitigate risks that unintended pharmaceuticals will be added to the insert 416. In an example embodiment, the door 420 of the cell 414 will unlock when identifying information associated with a pharmaceutical container is detected (e.g., by a pharmacist using a hand-held scanning device to read a bar code or other computer-readable element on the pharmaceutical container) that matches identifying information associated with the cell 414 (e.g., by a pharmacist using a hand-held scanning device to read a bar code or other computer-readable element on the face plate 418 of the insert 416) and information about the pharmacist who fills the cell 414 (e.g., by a pharmacist using a hand-held scanning device to read a bar code or other computer-readable element on the pharmacist's badge). The inserts 416 may be otherwise accessed to receive pharmaceuticals to be held and dispensed.

The cell 414 may be adapted to receive a funnel 602. A first portion 606 of the funnel 602 disposed within the cell 414 may be adapted to receive a dispensing tube 604 of the insert 416, through which pharmaceuticals may be dispensed from the insert 416 into the funnel 602. This may be through the large opening in the funnel 602. A second portion 608 of the funnel 602 may exist outside of the cell 414 and be in communication with a tube 502 connected to a rear opening 610 of the funnel 602, e.g., as illustrated in FIG. 6. The second portion 608 may be the stem of the funnel 602, which acts as a discharge for the pharmaceuticals being dispensed.

A frame portion 424 supports multiple tubes 502 connected to the discharge of the funnels 602 of the filling cabinet 402. For purposes of viewability, FIGS. 5 and 6 illustrate just two tubes 502. In general, however, the tubes 502 are included to enable the cells 414 to dispense drugs. The tubes 502 may be static dissipative flex tubes and may be grounded to allow for static to flow to ground the tubes 502.

The prefill assembly 404 includes multiple buffer tubes 426. Each of the tubes 502 is connected to a buffer tube 426 of the prefill assembly 404. The buffer tube 426 may be removable to, for example, facilitate cleaning or replacement. The buffer tube 426 may be shaped as a long-draw funnel or include a long-draw funnel. A long draw funnel may facilitate dispensing of pharmaceuticals while minimizing jams. In an example embodiment, a long draw funnel may be greater than six inches in length, greater than a foot in length, or greater than two feet in length and decrease in diameter over at least a portion of its length. However, the long draw funnel will maintain a diameter than will allow a pharmaceutical to pass therethrough.

The pharmaceuticals may be dispensed from the buffer tube 426 into a container 304 disposed on the pallet 302 when the container 304 is held under the buffer tube 426 within the pallet assembly 406.

Figure 7:
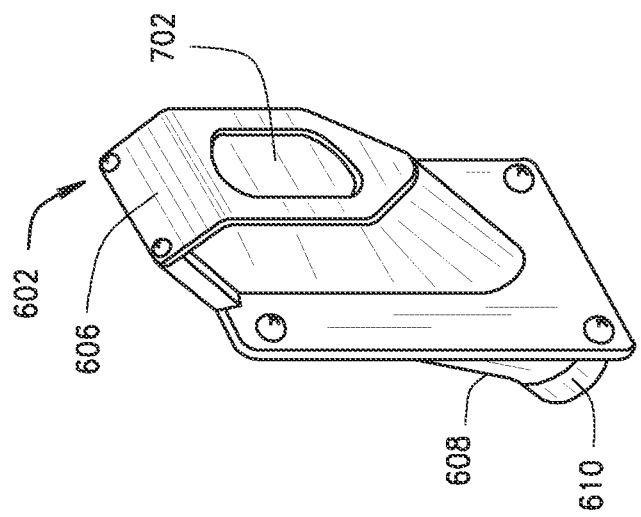
FIG. 7 is a side perspective view of a funnel that may be deployed in a filling cabinet of an automated dispensing subsystem, according to an example embodiment.

FIG. 7 illustrates a funnel 602 that may be disposed within a cell 414. The first end 606 may include a funnel gate 702. The funnel 602 may be made of plastic, metal, polymer, and/or other suitable materials. The funnel gate 702 may be open when the insert 416 is in the cell 414. For example, the dispensing tube 604 of the insert 416 may engage and open the funnel gate 702 when the insert is inserted into the cell 414. The funnel gate 702 may be weighted or biased such that it will shut when the insert 416 is pull out or removed from the cell 414 of the filling cabinet 402, for example to be cleaned or replaced. Thus, the funnel gate 702 may prevent pharmaceuticals from dropping through the funnel 602 (for example, into the tube 502) when the insert 416 is pulled out or removed from the cell 414.

In an example embodiment, the funnel 602 may be between approximately 8 inches and approximately 10 inches long, as measured from the top of the funnel gate 702 to the rear opening 610 of the funnel 602. For example, the funnel 602 may be approximately 9, 9.1, 9.2, 9.3, 9.4, 9.5, 9.6, 9.7, 9.8, 9.9 or 10 inches long. The width of the discharge end of the funnel 602 (which may be a diameter if the funnel 602 is substantially circular) may be between approximately 1 and approximately 2 inches. In an example embodiment, the discharge end of the funnel 602 may have an interior diameter of approximately 1.3 inches and an exterior diameter of approximately 1.5 inches.

The funnel 602 may be formed and/or placed within the cell 414 such that the connections between the dispensing tube 604 of the insert 416 and the funnel 602 (e.g., when the dispensing tube 604 engages the funnel gate 702) and between the tube 502 and the discharge end of the funnel 602 are tight. Such connections may be tight when any gap or space between the connections is smaller than the smallest drug that may be dispensed through the funnel 602. For example, tolerances for any such gap or space may be less than one millimeter.

Figure 8:
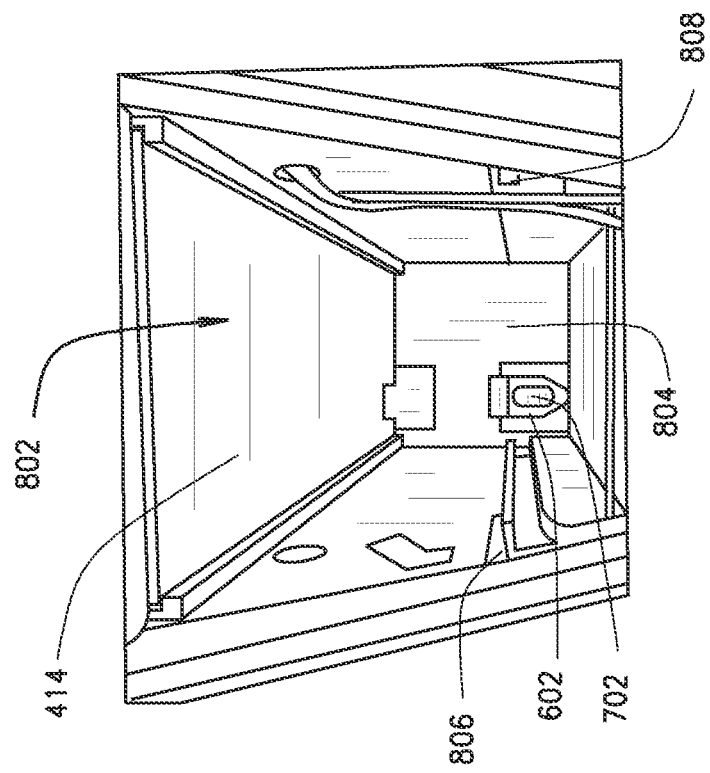
FIG. 8 is an interior view of a cell that may be deployed in a filling cabinet of an automated dispensing subsystem, according to an example embodiment.

FIG. 8 illustrates the inside 802 of the cell 414. The funnel 602 with the funnel gate 702 is disposed at a back wall 804 of the inside 802 of the cell 414. The funnel gate 702 is in the closed position in FIG. 8. The cell 414 is adapted to receive the insert 416 slid into the cell 414 along rails 806, 808. When inserted into the cell 414, the dispensing tube 604 of the insert 416 may engage and push open the funnel gate 702.

Figure 9:
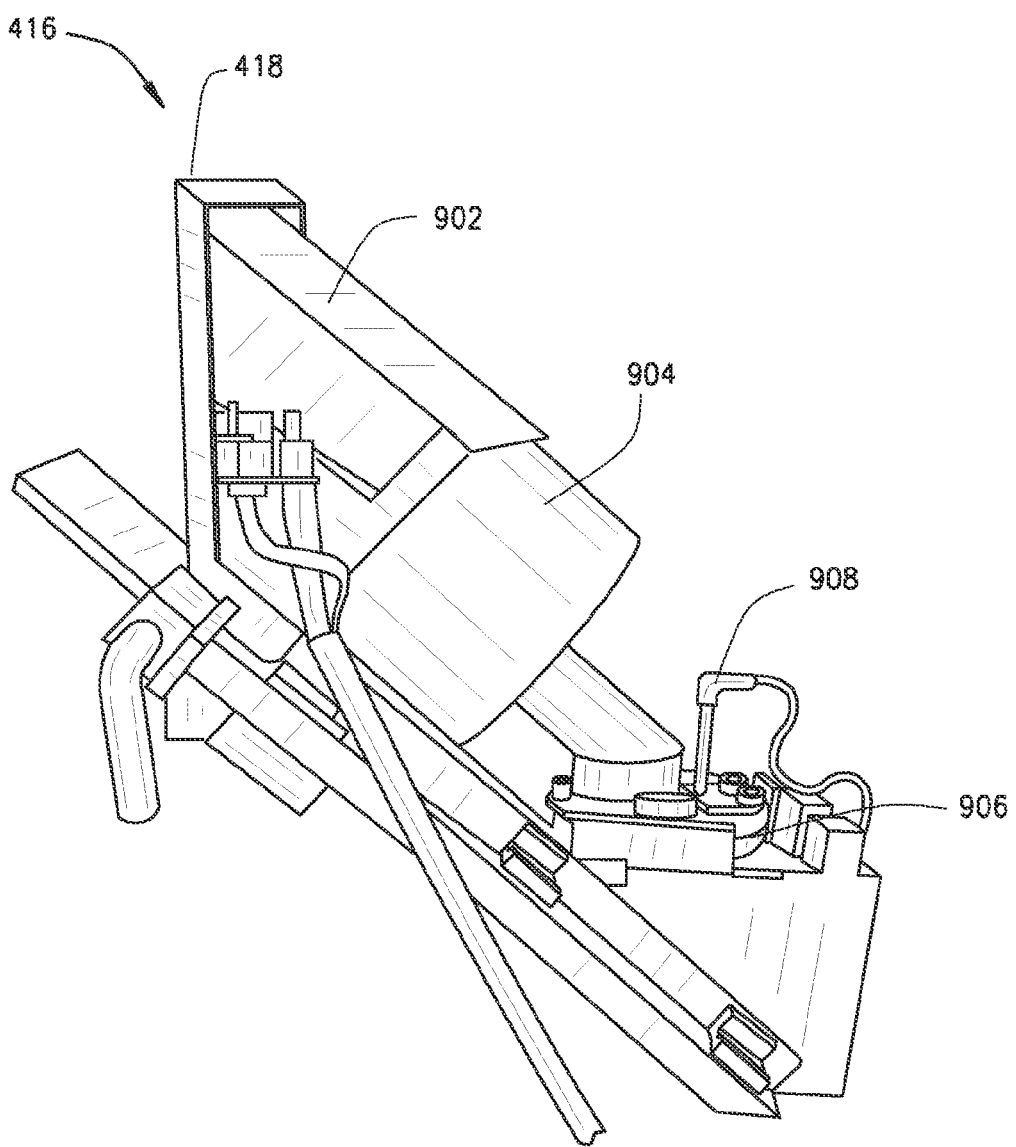
FIG. 9 is a view of an insert that may be deployed in a filling cabinet of an automated dispensing subsystem, according to an example embodiment.

FIG. 9 illustrates an insert 416 according to an example embodiment. A chute 902 may be in communication with the door 420 on the face plate 418 of the insert to receive pharmaceuticals, e.g., when the insert 416 is filled by a pharmacist as described above. The chute 902 may empty into a rotating hopper 904 in communication with a vibratory bowl 906. A level sensor 908 may be adapted to receive information about the quantity of pharmaceuticals in the vibratory bowl 906 and/or the hopper 904. Signals from the level sensor 908 may cause the hopper to spin to release additional quantities of pharmaceuticals into the vibratory bowl 906 and/or to stop spinning.

The insert 416 may employ vibratory technologies to facilitate a rapid dispensing stream of pharmaceuticals from the insert 416 into the funnel 602. The insert 416 may be adapted to count pharmaceuticals as they exit the vibratory bowl 906. Pharmaceuticals may be counted via a scanner array through which the pharmaceuticals pass as they exit the vibratory bowl 906. Pharmaceuticals may be otherwise counted. In an example embodiment, the insert 416 is a counting cell canister manufactured by Kirby Lester, LLC. Other devices may be used to perform the functions of an insert 416.

Counted pharmaceuticals (for example, a number of pharmaceuticals to be dispensed in accordance with a prescription) may be dispensed from the vibratory bowl 906 through the open funnel gate 702 of the funnel 602 into the tube 502.

Figure 10:
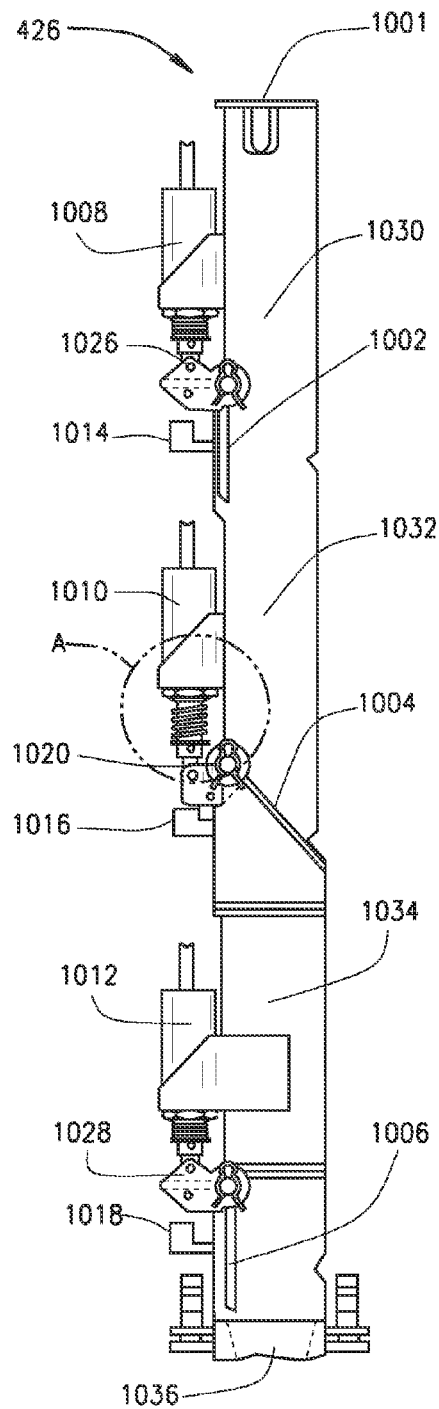
FIG. 10 is a side view of a buffer tube that may be deployed within the automated dispensing subsystem of FIG. 4, according to an example embodiment.

FIG. 10 illustrates the buffer tube 426 according to an example embodiment. The buffer tube 426 may be deployed in the prefill assembly 404, connected to an exit from the insert 416 (e.g., via tube 502), or may otherwise be used. The buffer tube may be adapted to receive, retain, and release a measured quantity of a pharmaceutical, in connection with dispensing the pharmaceutical into a container 304 to fill a prescription for the pharmaceutical.

An opening 1001 at the top of the buffer tube 426 is adapted to receive the tube 502 connected to the rear opening 610 (exit or lower opening) of a particular funnel 602 disposed in a particular cell 414. Thus, a particular buffer tube 426 is associated with a particular cell 414; pharmaceuticals dispensed from the insert 416 of the cell 414 will exit the cell 414 through the funnel 602, pass into the tube 502, and enter the buffer tube 426 at the opening 1001.

Measured quantities of pharmaceuticals dispensed from the insert 416 of the cell 414 connected to the buffer tube 426 may be staged by the buffer tube 426 for dispensing into containers 304. In general, measured quantities of pharmaceuticals represent exact counts of pills or other masses of pharmaceuticals.

The buffer tube 426 may include a first buffer tube gate 1002, a second buffer tube gate 1004, and a third buffer tube gate 1006. In other embodiments, more than three buffer tube gates may be included in a buffer tube; yet other embodiments of a buffer tube 426 include fewer than three buffer tube gates. For example, a buffer tube 426 may have one buffer tube gate. The number of buffer tube gates may vary based on the use or uses for which the buffer tube 426 is deployed.

A first solenoid 1008, a second solenoid 1010, and a third solenoid 1012, respectively, may be adapted to open and close the buffer tube gates 1002, 1004, 1006, respectively, in response to a communication from a first switch 1014, a second switch 1016, and a third switch 1018, respectively. The buffer tube gates 1002, 1004, 1006 may flutter to facilitate movement of pharmaceuticals through the gates 1002, 1004, 1006 and into the holding areas 1030, 1032, 1034 or a container 304, as applicable. For example, the buffer tube gates 1002, 1004, 1006 may flutter by opening and closing in quick succession, e.g., once, twice, three times, or more than three times.

The first buffer tube gate 1002, when closed, may retain pharmaceuticals within a first holding area 1030; the second buffer tube gate 1004, when closed, may retain pharmaceuticals within a second holding area 1032; and the third buffer tube gate 1006, when closed, may retain pharmaceuticals within a third holding area 1034.

The first and second buffer tube gates 1002, 1004, when open, may release pharmaceuticals from the holding areas 1030, 1032, respectively, into the next holding area 1032, 1034, respectively. The third buffer tube gate 1006, when open, may release pharmaceuticals from the third holding area 1034, through a buffer tube exit 1036, into a container 304 on the pallet 302 in the pallet assembly 406. When in use, a buffer tube 426 having a plurality of gates may have only one gate open at a time. Alternatively more than one gate may open simultaneously or substantially simultaneously, e.g., if there are no measured quantities of pharmaceuticals in either of the holding areas 1030, 1032, both the buffer tube gates 1002, 1004 may be opened such that the pharmaceuticals dispense directly into holding area 1034, or all buffer tube gates 1002, 1004, 1006 may be open such that the measured quantity of pharmaceuticals dispenses from the cell 414 directly through the buffer tube exit 1036 into the container 304.

The buffer tube 426 may be employed to stage dispensing of measured quantities of pharmaceuticals received from the cell 414 connected to the buffer tube 426. For example, a first measured quantity of pharmaceuticals to be dispensed according to a prescription may be retained in the first holding area 1030, a second measured quantity of pharmaceuticals to be dispensed according to a prescription may be retained in the second holding area 1032, and a third measured quantity of pharmaceuticals to be dispensed according to a prescription may be retained in the third holding area 1034.

In some instances, the first, second, and/or third measured quantities of pharmaceuticals may be portions of the entire quantity of pharmaceuticals to be dispensed in accordance with a particular prescription, such as a prescription for a number of pills or tablets that exceeds the quantity of pills or tablets suitable for a container 304 used in the system 100.

In other instances, each of the first, second, and/or third measured quantities may be associated with a different prescription and such measured quantities may be the entire quantity of pharmaceuticals associated with such particular prescriptions. For example, the first, second, and/or third measured quantities of pharmaceuticals may each represent a 30 day supply of drugs. These staged drugs may be each be dispensed in separate, individual containers 304 to supply 30 day fills, may be dispensed into a single container 304 to supply a 90 day fill, or otherwise.

The buffer tube 426 and/or one or more of the holding areas 1030, 1032, 1034 may hold a volume consistent with the capacity of the container 304 used in the system 100. For example, the buffer tube 426 and/or one or more of the holding areas 1030, 1032, 1034 may hold a volume of approximately 200 cc. In other embodiments, the volume may be more than 200 cc or less than 200 cc.

Figure 11:
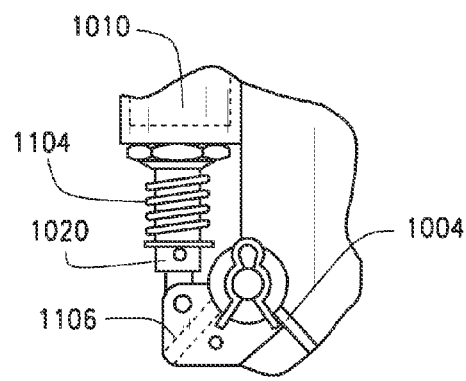
FIG. 11 is a view of a portion of the buffer tube of FIG. 12.

FIG. 11 is a close-up illustration of a portion of the second solenoid 1010 (at A of FIG. 10) when the buffer tube gate 1004 is in a closed position. As illustrated in FIG. 11, the second solenoid 1010 includes a spring-actuated plunger 1020. When a spring 1104 is at or near its free-length position (e.g., wherein minimal or no compressive load is imposed upon the spring 1104), the spring-actuated plunger 1020 engages an arm 1106 of the buffer tube gate 1004, thereby retaining the buffer tube gate 1004 in a closed position. When activated by the switch 1016, the solenoid 1010 compresses the spring 1022 by the spring-actuated plunger 1020 of the solenoid moving upward into (or toward) the body of the second solenoid 1010 and the second buffer tube gate 1004 will open. For example, spring-biased plungers 1026, 1028 of the solenoids 1008, 1012, respectively, are illustrated in the open-gate position in FIG. 10.

Figure 12:
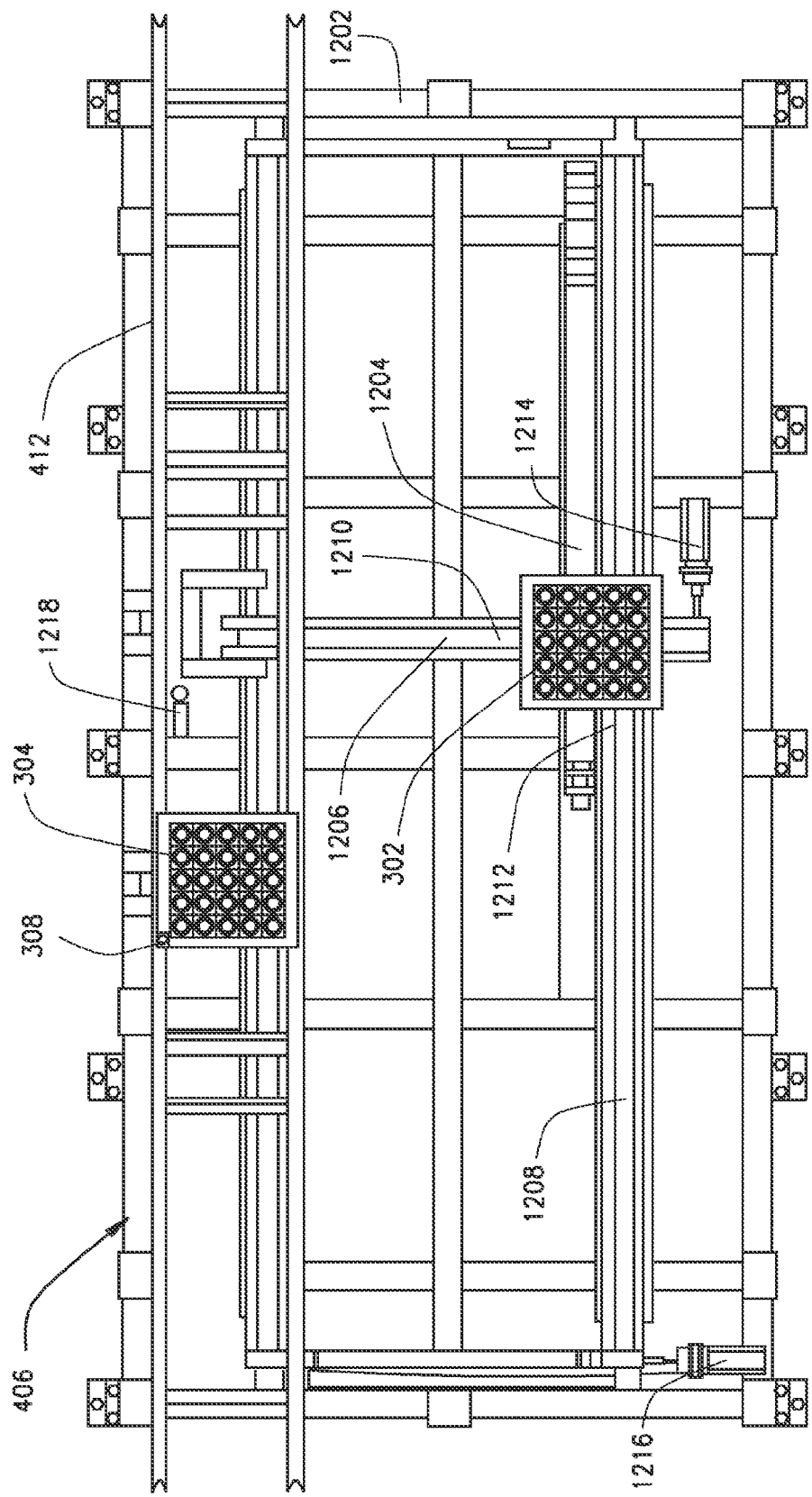
FIG. 12 is a top view of a pallet assembly of the automated dispensing subsystem of FIG. 4, according to an example embodiment.
Figure 13:
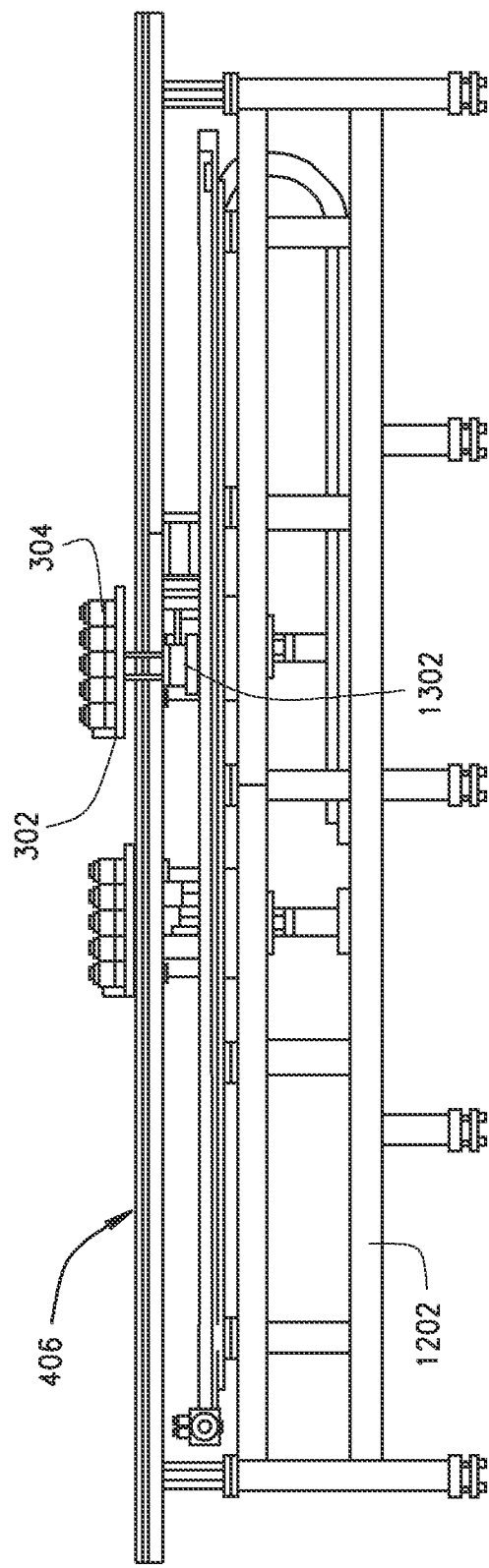
FIG. 13 is a side view of a pallet assembly of FIG. 12.

FIGS. 12 and 13 illustrate a top view and a side view, respectively, of the pallet assembly 406 of the automated dispensing subsystem 204, according to an example embodiment. A pallet assembly frame 1202 provides support in the pallet assembly 406, including the pallet conveyor 412 and an x-y movement apparatus 1204. The x-y movement apparatus 1204 moves the pallet 302 within the pallet assembly 406 of the automated dispensing subsystem 204. The x-y movement apparatus 1204 includes an x-component 1206 and a y-component 1208.

The x-component 1206, in operation, moves a pallet 302 in a direction perpendicular to the pallet conveyor 412. The x-component 1206 includes an x-axis support arm 1210 that supports the pallet 302 as it moves within the pallet assembly 406 and an x-component motor 1214 that actuates the x-component 1206 of the x-y movement apparatus 1204.

The y-component 1208, in operation, moves a pallet 302 in a direction parallel to the pallet conveyor 412. The y-component 1208 includes a y-axis support arm 1212 that supports the pallet 302 as it moves within the pallet assembly 406 and a y-component motor 1216 that actuates the y-component 1208 of the x-y movement apparatus 1204.

The x-y movement apparatus 1204 may engage and move a pallet 302 within the pallet assembly 406 of the automated dispensing subsystem 204 such that the containers 304 in the pallet 302 are moved below the buffer tubes 426 in communication with the cells 414 containing pharmaceuticals to be dispensed into such containers 304, via the system 100.

The pallet assembly 406 may include a lift apparatus 1302. The lift apparatus 1302 may engage the pallet 302 and lift it such that a container 304 on the pallet 302 is aligned to receive pharmaceuticals from the buffer tube 426 in communication with the cell 414 holding pharmaceuticals to be dispensed into that particular container 304. In an example, the container 304 is positioned directly (or substantially directly) below the buffer tube exit 1036 of the buffer tube 426 in communication with the cell 414 holding pharmaceuticals to be dispensed into that particular container 304. A container 304 may be positioned such that the opening of the container 304 is very close to the buffer tube exit 1036, e.g., less than approximately 0.01 inches, 0.009 inches, 0.008 inches, 0.007 inches, 0.006 inches, 0.005 inches, or 0.004 inches from the buffer tube exit 1036.

Pharmaceuticals may be dispensed from the buffer tube 426 into the container 304 when the appropriate container 304 is held under the buffer tube exit 1036 by the lift apparatus 1218 of the pallet assembly 406. In an example embodiment, such pharmaceuticals are held in held the third holding area 1034 of the buffer tube 426 and are dispensed into the container 304 when the third buffer tube gate 1006 is actuated by the third switch 1018. In another example embodiment, such pharmaceuticals are held in the first or second holding area 1030, 1032 of the buffer tube 426 when the container 304 is position below the buffer tube exit 1036 and released through the first and/or second buffer tube gates 1002, 1004 prior to being released through the third buffer tube gate 1006 and into the container 304.

The automated dispensing subsystem 204 may include an RFID reader 1218. The RFID reader 1218 may read data on the RFID tag 308 of the pallet 302 to obtain data associated with the particular pallet 302 and/or containers 304 within the pallet 302, such as order data 110, member data 112, claims data 114, drug data 116, prescription data 118, and/or plan sponsor data 120 associated with prescriptions (or portions of prescriptions) to be filled using containers 304 on that pallet 302. The RFID reader 1218 may write data to the RFID tag 308 of a pallet 302 (or otherwise cause data to be associated with the pallet 302), such as order data 110, member data 112, claims data 114, drug data 116, prescription data 118, and/or plan sponsor data 120 associated with pharmaceuticals dispensed into containers 304 on the pallet 302 via the automated dispensing device 130. Although only one RFID reader 1218 is illustrated on FIG. 12, more than one RFID reader 1218 may be employed in an automated dispensing subsystem 204. When more than one RFID reader 1218 is employed in an automated dispensing subsystem 204, each RFID reader 1218 may be adapted to read the RFID tag 308 on a pallet 302 at a different stage. For example, an RFID reader may read the RFID tags 308 of pallets as they queue for entry into the automated dispensing subsystem 204, another may read the RFID tags 308 of pallets as they enter the automated dispensing subsystem 204, and another may read the RFID tags 308 of pallets 302 as they exit the automated dispensing subsystem 204.

The RFID reader 1218 and/or another RFID reader may read the container identifiers of the containers on the pallet, the automated dispensing subsystem identifier, and the container properties of the containers on the pallet from the RFID tag 308 of a pallet 302 when it queues for entry into the automated dispensing subsystem 204 and may write the container identifiers of the containers 304 to be filled at the automated dispensing subsystem 204 and the identifiers of the particular cells from which the containers will be filled to the RFID tag 308 of the pallet 302. The RFID reader 1218 and/or another RFID reader may read the container identifiers of the containers 304 to be filled at the automated dispensing subsystem 204 and the identifiers of the particular cells from which the containers 304 will be filled from the RFID tag 308 of the pallet 302 when it enters the automated dispensing subsystem 204. The RFID reader 1218 and/or another RFID reader may read the pallet route within the system 100 and the pallet route within the automated dispensing subsystem 204 as it exits the automated dispensing subsystem 204 and may clear the pallet route within the automated dispensing subsystem 204 as it exits the automated dispensing subsystem 204 (e.g., to prevent the pallet 308 from re-entering the same automated dispensing subsystem 204 in an embodiment of the system 100 that employs more than one automated dispensing subsystem 204).

Figure 14:
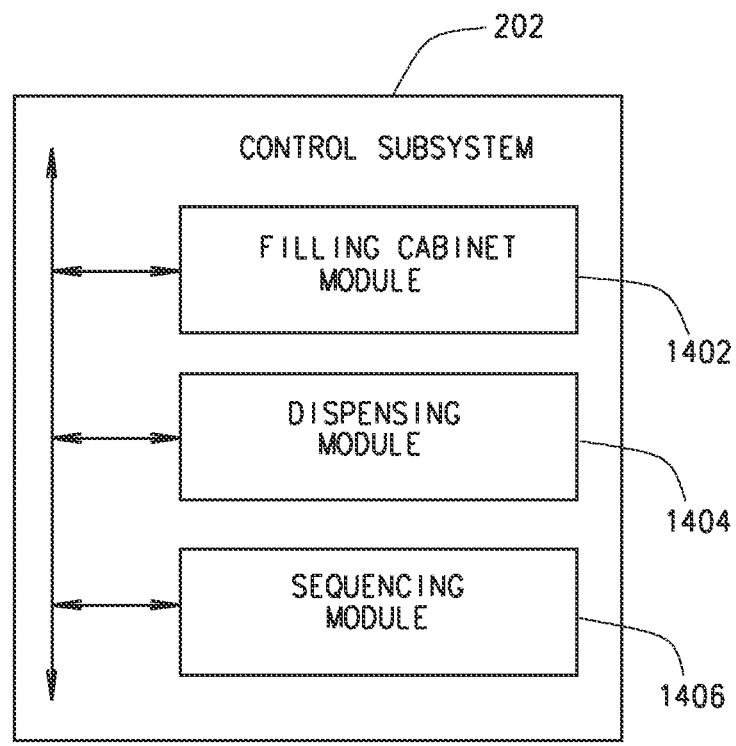
FIG. 14 is a diagram of a control subsystem that may be deployed within the automated dispensing device of FIG. 2, according to an example embodiment.

FIG. 14 illustrates an example control subsystem 202 that may be deployed in the order processing device 102, the automated dispensing device 130, or otherwise deployed in the system 100. One or more modules are communicatively coupled and included in the control subsystem 202 to enable control of the automated dispensing operations of the automated dispensing device 130. The modules of the control subsystem 202 that may be included are a filling cabinet module 1402, a dispensing module 1404, and a sequencing module 1406. Other modules may also be included.

In some embodiments, the modules of the control subsystem 202 may be distributed so that some of the modules are deployed in the order processing device 102 and some modules are deployed in the automated dispensing device 130. In one embodiment, the modules are deployed in memory and executed by a processor coupled to the memory. The functionality contained within the modules 1402-1406 may be combined into a lesser number of modules, further divided among a greater number of modules, or redistributed among existing modules. Other configurations including the functionality of the modules 1402-1406 may be used.

The filling cabinet module 1402 may track quantities of pharmaceuticals placed into the insert 416 in the cell 414 and dispensed from the insert 416. The filling cabinet module 1402 may control operations of the filling cabinet 402. For example, the filling cabinet module 1402 may generate an alert when the quantity of pharmaceuticals in the insert 416 has dropped below a pre-determined level. The level at which an alert is be generated may be dependent upon parameters specific to the particular pharmaceutical, e.g., based on factors such as the size of the pharmaceutical, the typical prescribed quantity of the pharmaceutical, the relative popularity of the pharmaceutical, or other factors. For example, an alert may be generated if the quantity of pharmaceutical is below about 100 units (e.g., pills, capsules or tablets), below about 150 units, below about 200 units, below about 250 units, below about 300 units, or below about 350 units. Other types of thresholds may be used. Regardless of whether an alert has been generated, pharmaceuticals may continue to be dispensed from the insert 416 until it is empty. Alerts generated by the filling cabinet module 1402 may be prioritized. For example, alerts may be prioritized based on criterion such as general popularity of the pharmaceutical held in the cell 414, pending orders in the system 100 for such pharmaceutical, quantity of pharmaceuticals remaining in the cell 414, combinations thereof, or may be otherwise prioritized. The filling cabinet module 1402 may identify a particular cell 414 as being unavailable to the automated dispensing subsystem 204 when the insert 416 is pulled out or removed from the cell 414 of the filling cabinet 402.

The dispensing module 1404 may access data, such as the order data 110, the member data 112, the claims data 114, the drug data 116, the prescription data 118, and/or the plan sponsor data 120, associated with a particular pallet 302. Data may be accessed from the RFID tag 308 of the pallet 302, the sequencing module 1406, or the database 108, for example. Based on such data, the dispensing module 1404 may identify the quantity of pharmaceuticals within a particular cell 414 to be dispensed into a particular container 304 on a particular pallet 302 and may control the operations of the inserts 416 and/or the buffer tubes 426 and/or may otherwise control the operations of the automated dispensing subsystem 204 to cause pharmaceuticals to be dispensed from a cell 414 and, ultimately, into the container 304 on the pallet 302. The dispensing module 1404 may receive the container identifiers of the containers 304 to be filled at the automated dispensing subsystem 204 and may return the identifiers of the cells 414 from which the containers 304 will be filled, the identifier of the automated dispensing subsystem 204, the dispense type, and the dispense quantity.

For example, the dispensing module 1404 may cause the hopper 904 of the insert 416 disposed within the cell 414 to rotate, it may cause the vibratory bowl 906 of the insert 416 to vibrate, it may count pharmaceuticals as they exit the vibratory bowl 906 into the funnel 602, it may cause the vibratory bowl 906 to cease vibrating after a particular quantity of pharmaceuticals has been counted by the counter, and/or it may otherwise initiate one or more than one operations of the filling cabinet 402 to cause a particular quantity of pharmaceuticals to be dispensed from the insert 416 into the buffer tube 426 associated with that particular cell 414.

The dispensing module 1404 may control operations of the buffer tubes 426 of the prefill assembly 404. The dispensing module 1404 may control the operations of one or more than one of the switches 1014, 1016, 1018 to cause a quantity of pharmaceuticals dispensed from the insert 416 of the cell 214 to be retained within a particular holding area 1032, 1034, 1036 or released from a particular holding area into the next holding area or into the container 304, as the case may be. For example, the dispensing module 1404 may engage the third switch 1018 to cause the third buffer tube gate 1006 to open, thereby releasing the contents of the third holding area 1034 into the container 304 disposed below the opening 1036 of the buffer tube 426. The dispensing module 1404 may then engage the second switch 1016 to cause the second buffer tube gate 1004 to open, thereby releasing the contents of the second holding area 1032 into the third holding area 1034.

Thus, in this example, embodiment, up to three prescriptions (or portions of prescriptions) may be retained within the holding areas 1032, 1034, 1036 of the buffer tube 426 in preparation for dispensing into the container 304, thereby reducing the amount of time necessary to fill the container 304 with the measured quantity of pharmaceuticals after it has been placed below the opening 1036 of the buffer tube 426 (for example, as compared to a subsystem in which pharmaceuticals are not counted until the container 304 had been positioned to receive the pharmaceuticals). In an example embodiment, the three prescriptions in the holding areas 1032, 1034, 1036 may hold differing quantities of pharmaceuticals.

The sequencing module 1406 may accesses data, such as the order data 110, the member data 112, the claims data 114, the drug data 116, the prescription data 118, and/or the plan sponsor data 120, associated with a particular pallet 302. Data may be accessed from the RFID tag 308 of a pallet 302 or the database 108, for example. Data associated with a particular pallet may be accessed by an RFID reader 1218 of the automated dispensing subsystem 204 or may be otherwise accessed. Based on such data, the sequencing module 1406 may determine which cells 414 within the automated dispensing subsystem 204 to dispense associated pharmaceuticals into the containers 304 on the particular pallet 302. The sequencing module 1406 may determine the sequence in which the particular pallet 302 will move between dispensing positions associated with such cells 414 (e.g., underneath the openings 1036 of the buffer tubes 426). The sequence may be selected based on factors such as proximity of the cells 414 and/or the buffer tubes 426 from which containers 304 on the pallet 302 will be filled, availability or likely availability of a particular cell 414 (for example, as determined based on whether an alert has been generated for the particular cell 414 by the filling cabinet module 1402, or otherwise generated, and/or the level of such alert), and/or other factors.

The sequence may be selected to minimize wait time at the cell 414. For example, the sequence may be selected (and the operations of the automated processing subsystem 204 may be controlled) such that the container 304 to be filled with a pharmaceutical from the cell 414 arrives at the dispensing position associated with such cell 414 after the pharmaceutical to be dispensed into the container 304 is in a particular holding area of the buffer tube 426 in communication with the cell 414, such as at least the third holding area 1034, at least the second holding area 1032, or at least the first holding area 1032. By way of further example, if the pallet 302 includes more than one container 304 to be filled with a particular pharmaceutical, the sequencing module 1406 may order the filling of the containers on the pallet 302 such that a first container is filled with pharmaceuticals dispensed from the buffer tube 426 in communication with the cell 414 containing the pharmaceutical at a first time and a second container is filled with pharmaceuticals dispensed from such buffer tube 426 at a second time, and wherein at least one other container is filled from the buffer tube 426 in communication with a different cell 414 between the filling of the first container 304 and the second container 304.

If the automated dispensing subsystem 204 includes more than one cell 414 with a particular pharmaceutical, then in such an embodiment, the sequencing module 1406 may determine which of such cells 414 will be used to dispense such pharmaceutical. For example, the sequencing module 1406 may identify a first cell 414 from which a first container 304 will be filled with that particular pharmaceutical and a second cell 414 from which a second container 304 will be filled with that particular pharmaceutical. Other factors may be used to establish the sequence in which the containers 304 in a particular pallet 302 will be filled.

Multiple automated filling subsystem 204 may be deployed in the automated filling device 130 of the system 100. In such an embodiment, one or more of the modules 1402-1406 of the control subsystem 202 and/or the order processing device 102 may determine which one or more automated filling subsystem 204 will be used to fill the containers 304 on a particular pallet 302 and may control the operations of the one or more automated filling subsystems 204 and/or the system 100 to cause pharmaceuticals to be dispensed into the containers 304 on such pallet 302 from cells 414 of such one or more than one automated filling subsystems 204.

Figure 15:
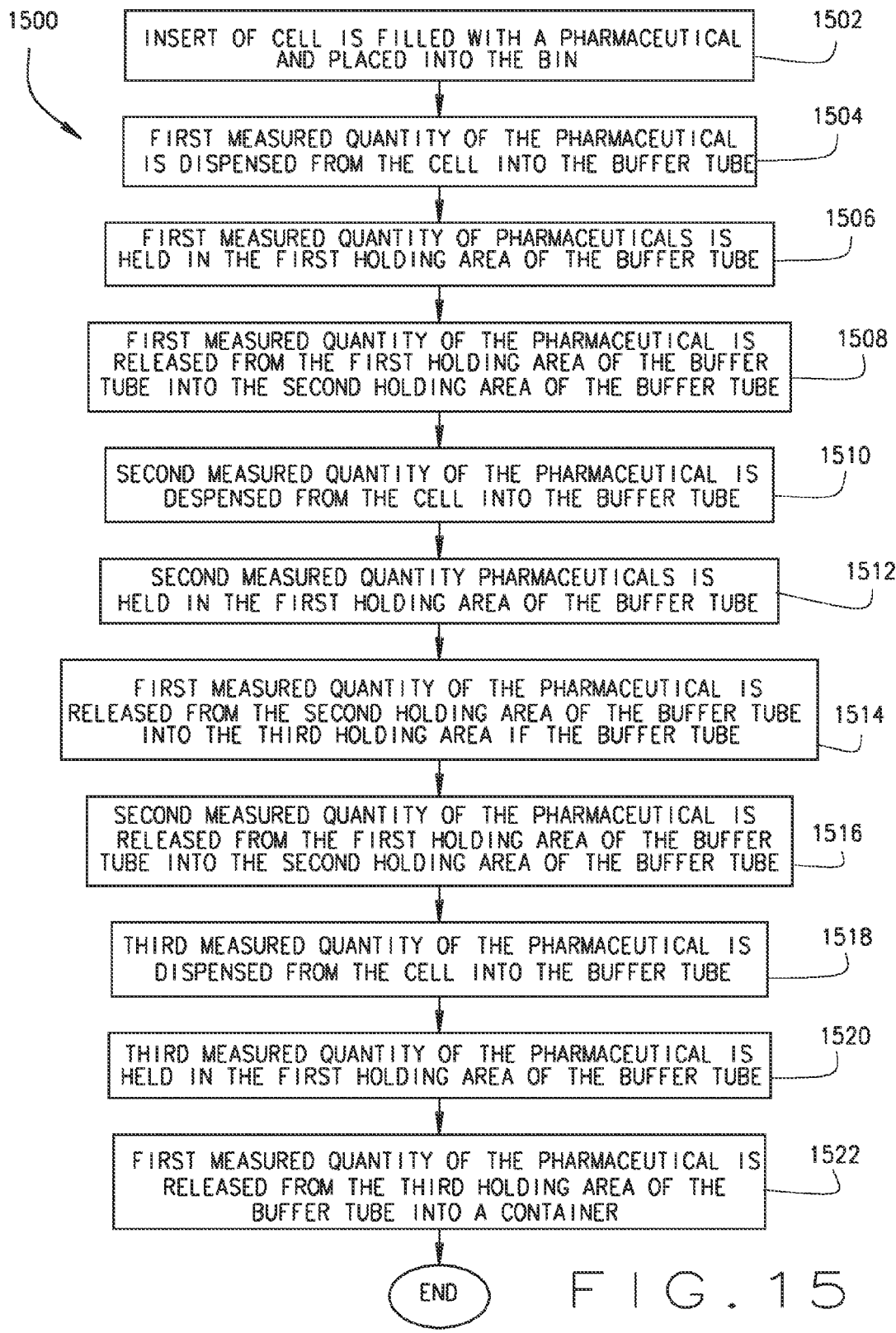
FIG. 15 is an example process flow illustrating a method of configuring a pallet, according to an example embodiment.

FIG. 15 illustrates a method 1500 for dispensing pharmaceuticals into the container 304, according to an example embodiment. The method 1500 may be performed by the automated dispensing device 130, partially by the order processing device 102 and partially by the automated dispensing device 130, or may be otherwise performed.

At block 1502, the insert 416 of the cell 414 is filled with a particular pharmaceutical. At block 1504, a first measured quantity of the pharmaceutical is dispensed from the cell 414 into the buffer tube 426 connected to the cell 414 via the tube 502. At block 1506, the first measured quantity of pharmaceuticals is held within the first holding area 1030 of the buffer tube. At block 1508, the first measured quantity of the pharmaceutical is released by the first buffer tube gate 1002 into the second holding area 1032 of the buffer tube 426. A second measured quantity of the pharmaceutical is dispensed from the cell 414 into the buffer tube 426 at block 1510 and, at block 1512, is held within the first holding area 1030. The first measured quantity of the pharmaceutical is released by the second buffer tube gate 1004 into the third holding area 1034 of the buffer tube 426 at block 1514, the second measured quantity of the pharmaceutical is released by the first buffer tube gate 1002 into the second holding area 1032 of the buffer tube 426 at block 1516, and a third measured quantity of the pharmaceutical is dispensed from the cell 414 into the buffer tube 426 at block 1518. At block 1520, the third measured quantity of pharmaceuticals is held within the first holding area 1030. At block 1522, the first measured quantity of pharmaceuticals is released by the third buffer tube gate 1006 from the third holding area 1034 into the container 304 aligned to receive the first measured quantity of pharmaceuticals from the buffer tube 426.

Figure 16:
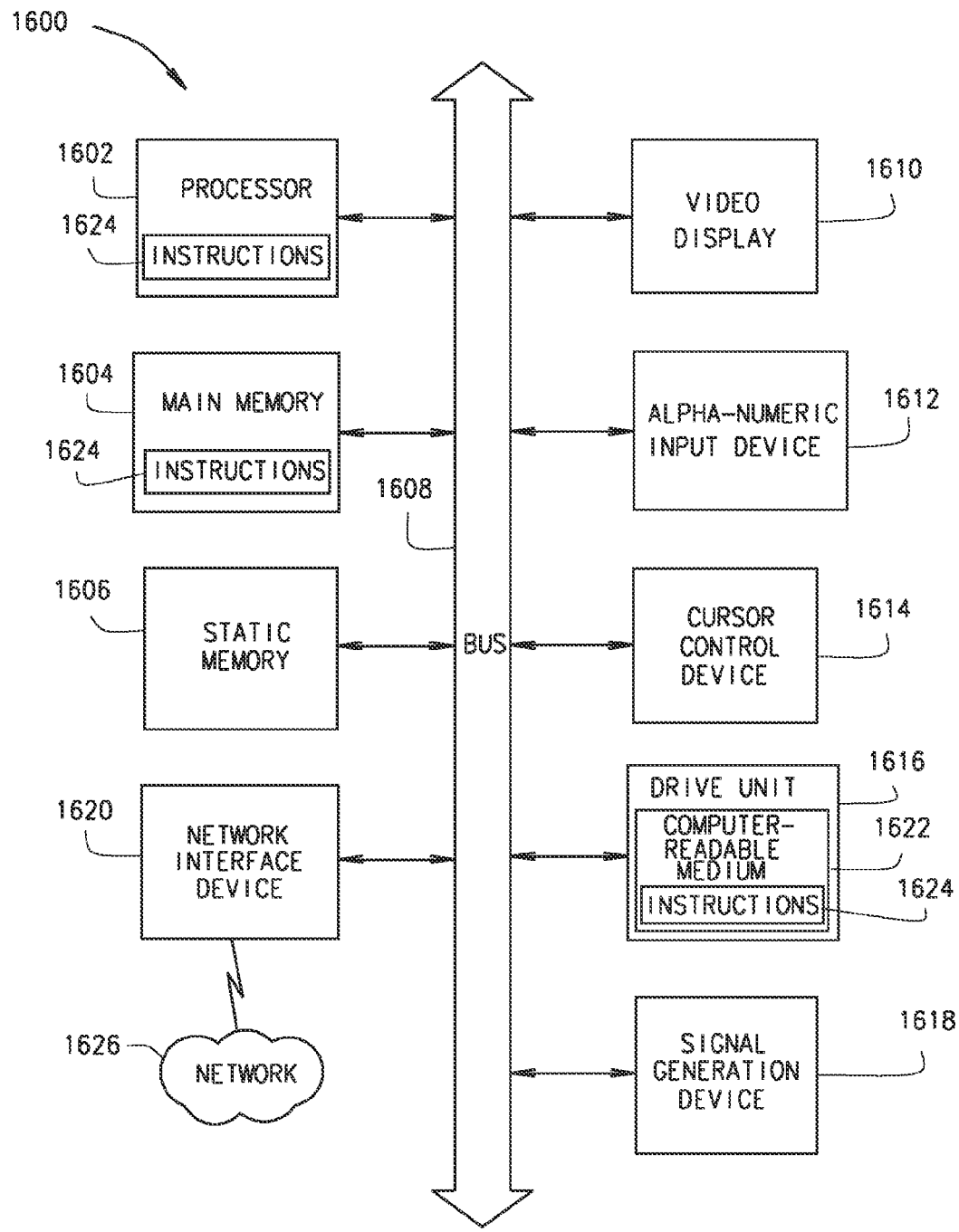
FIG. 16 is a block diagram of a machine in the example form of a computer system within which a set of instructions for causing the machine to perform any one or more of the methodologies discussed herein may be executed or stored.

FIG. 16 shows a block diagram of a machine in the example form of a computer system 1600 within which a set of instructions may be executed causing the machine to perform any one or more of the methods, processes, operations, or methodologies discussed herein. The devices 102, 106, 122-144 may include the functionality of the one or more computer systems 1600.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions sequential or otherwise) that specifies actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1600 includes a processor 1602 (e.g., a central processing unit (CPU) a graphics processing unit (GPU) or both), a main memory 1604 and a static memory 1606, which communicate with each other via a bus 1608. The computer system 1600 further includes a video display unit 1610 (e.g., a liquid crystal display (LCD) or a cathode ray tube (CRT)). The computer system 1600 also includes an alphanumeric input device 1612 (e.g., a keyboard), a cursor control device 1614 (e.g., a mouse), a drive unit 1616, a signal generation device 1618 (e.g., a speaker) and a network interface device 1620.

The drive unit 1616 includes a computer-readable medium 1622 on which is stored one or more sets of instructions (e.g., software 1624) embodying any one or more of the methodologies or functions described herein. The software 1624 may also reside, completely or at least partially, within the main memory 1604 and/or within the processor 1602 during execution thereof by the computer system 1600, the main memory 1604 and the processor 1602 also constituting computer-readable media.

The software 1624 may further be transmitted or received over a network 1626 via the network interface device 1620.

While the computer-readable medium 1622 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

In an example embodiment, a pharmaceutical order filling system includes an order processing device that receives a pharmaceutical order, an automated dispensing device that includes a filling cabinet with a cell containing an available quantity of a pharmaceutical to be dispensed according to the pharmaceutical order. The system also includes a prefill assembly with a buffer tube that is in communication with the cell of the filling cabinet and that is configured to stage dispensing of measured quantities of pharmaceuticals, wherein the automated dispensing device is communicatively coupled to the order processing device and configured to dispense a first measured quantity of the available quantity of the pharmaceutical into the buffer tube and to dispense the first measured quantity of the pharmaceutical from the buffer tube into a container.

In another example embodiment, a pharmaceutical order filling system includes an automated dispensing device in which a filling cabinet, a prefill assembly and a pallet assembly cooperatively communicate. The filling cabinet includes a plurality of cells, each of which contains a quantity of a particular pharmaceutical, the prefill assembly includes a plurality of buffer tubes, each buffer tube of the plurality of buffer tubes being in respective communication with a particular cell of the plurality of cells, and the pallet assembly includes an x-y movement apparatus adapted to engage and move a pallet within the pallet assembly, wherein a plurality of containers are disposed on the pallet. In this example embodiment, the automated dispensing device is configured to dispense a measured quantity of a pharmaceutical from one of the cells into a holding area of a buffer tube uniquely associated with that cell and to dispense the measured quantity of the pharmaceutical from the holding area of the buffer tube into a container positioned below the buffer tube.

In yet another example embodiment, a pharmaceutical order filling system includes an order processing device to receive pharmaceutical orders prescribing a plurality of pharmaceuticals, an automated dispensing device that is cooperatively coupled to the order processing device. The automated dispensing device includes a filling cabinet, a prefill assembly, and a pallet assembly. The filling cabinet includes a plurality of cells, one of which contains a quantity of one of the pharmaceuticals. The system also includes a sequencing module to determine an order for dispensing a measured quantity of each of the plurality of pharmaceuticals into a plurality of containers.

The inventive subject matter may be represented in a variety of different embodiments of which there are many possible permutations.

Thus, methods and systems for automated pharmaceutical dispensing have been described. Although embodiments of the present invention have been described with reference to specific example embodiments, it will be evident that various modifications and changes may be made to these embodiments without departing from the broader spirit and scope of the embodiments of the invention, Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion.

The invention claimed is:

1. A pharmaceutical order filling system comprising:
   an order processing device to receive a pharmaceutical order; and
   an automated dispensing device comprising
   a filling cabinet including a cell containing an available quantity of a pharmaceutical of the pharmaceutical order,
   a prefill assembly including a buffer tube that is in communication with the cell of the filling cabinet and that is configured to stage dispensing of a plurality of measured quantities of the pharmaceutical,
   wherein the automated dispensing device is communicatively coupled to the order processing device and configured to dispense a first measured quantity of the available quantity of the pharmaceutical into the buffer tube and to dispense the first measured quantity of the pharmaceutical from the buffer tube into a container, wherein the first measured quantity is selected from the plurality of measured quantities, and
   wherein the cell comprising a funnel, wherein the cell is adapted to receive an insert, the insert being adapted to receive the available quantity of the pharmaceutical and to dispense the first measured quantity of the pharmaceutical through a dispensing tube of the insert, and the funnel comprising a weighted gate adapted to receive the dispensing tube of the insert.

2. The system of claim 1, wherein the system further comprises a pallet assembly and wherein the filling cabinet is physically housed above the prefill assembly and the prefill assembly is located above the pallet assembly, and wherein the filling cabinet is on a first, upper floor of a structure and the pallet assembly is on a second, lower floor of the structure.

3. The system of claim 1, further comprising:
a tube that connects a stem opening of the funnel to an opening of the buffer tube.

4. The system of claim 1, wherein the insert includes a door configured to unlock to receive the available quantity of the pharmaceutical in response to a communication from the order processing device,
wherein the communication from the order processing device is generated when an insert code on a face plate of the insert corresponds to a container code on the container.

5. The system of claim 4, wherein the insert code corresponds to the container code when the insert code and the container code are both associated with a same pharmaceutical.

6. The system of claim 1, wherein the buffer tube comprises a holding area adapted to receive, retain, and release the first measured quantity of the pharmaceutical.

7. The system of claim 6 wherein the holding area comprises a first holding area and a second holding area,
wherein the first holding area is adapted to receive, retain, and release the first measured quantity of the pharmaceutical,
wherein the automated dispensing device is further configured to release the first measured quantity of the pharmaceutical from the first holding area into the second holding area and to dispense a second measured quantity of the pharmaceutical into the first holding area of the buffer tube after the first measured quantity of the pharmaceutical has been released into the second holding area.

8. The system of claim 1, wherein the automated dispensing device is configured to generate an alert when the available quantity of the pharmaceutical in the cell is less than a pre-determined level.

9. The system of claim 1, wherein the system further comprises a pallet assembly, wherein the container is disposed on a pallet, and wherein a pallet assembly comprises an x-y movement apparatus adapted to engage and move the pallet within the pallet assembly such that the container is positioned below the buffer tube to receive the first measured quantity of the pharmaceutical.

10. The system of claim 9, wherein an opening of the container is less than approximately 0.01 inches from a buffer tube exit of the buffer tube when the first measured quantity of the pharmaceutical is dispensed into the container.

11. The pharmaceutical order filling system of claim 1 further comprising:
a sequencing module to determine an order for dispensing each of the plurality of measured quantities of the pharmaceutical into the container.

12. The system of claim 11, wherein the buffer tube is adapted to receive and retain the plurality of measured quantities of the pharmaceutical dispensed from the cell in communication with the buffer tube.

13. A pharmaceutical order filling system comprising:
an automated dispensing device cooperatively comprising
a filling cabinet including a plurality of cells, each cell of the plurality of cells containing a quantity of a pharmaceutical selected from a plurality of pharmaceuticals,
a prefill assembly including a plurality of buffer tubes, each buffer tube of the plurality of buffer tubes being in respective communication with a particular cell of the plurality of cells,
a pallet assembly including an x-y movement apparatus adapted to engage and move a pallet within the pallet assembly, wherein a plurality of containers are disposed on the pallet, and
a first cell of the plurality of cells comprising a funnel, wherein the first cell is adapted to receive an insert comprising a dispensing tube, and wherein the dispensing tube is adapted to engage and push open a funnel gate of the funnel when the insert is in the cell, and
wherein the automated dispensing device is configured to dispense a first measured quantity of a first pharmaceutical from the first cell into a first holding area of a first buffer tube uniquely associated with the first cell and to dispense the first measured quantity of the first pharmaceutical from the first holding area of the first buffer tube into a first container when the first container is positioned below the first buffer tube, wherein the first pharmaceutical is among the plurality of pharmaceuticals, the first cell is among the plurality of cells, the first buffer tube is among the plurality of buffer tubes, and the first container is among the plurality of containers.

14. The system of claim 13 wherein the first buffer tube further comprises a second holding area and wherein the automated dispensing device is further configured to release the first measured quantity of the first pharmaceutical into the second holding area and to dispense a second measured quantity of the first pharmaceutical into the first holding area of the first buffer tube after the first measured quantity of the first pharmaceutical has been released into the second holding area.

15. The system of claim 13 wherein each of the plurality of buffer tubes is shaped as a long-draw funnel.

16. The system of claim 13 wherein the insert comprises a hopper, a vibratory bowl, and a level sensor, wherein the level sensor is configured to cause the hopper to spin and to release a released quantity of the first pharmaceutical into the vibratory bowl 906, wherein the released quantity of the first pharmaceutical comprises at least a portion of the first measured quantity of the first pharmaceutical.

17. The system of claim 13 wherein the first buffer tube comprises a buffer tube gate configured to release the first measured quantity of the first pharmaceutical from the first holding area, wherein the buffer tube gate is configured to flutter by opening and closing in quick succession.

18. The system of claim 13 wherein the pallet assembly comprises a lift apparatus configured to the pallet and lift the pallet such that the first container is aligned to receive the first measured quantity of the first pharmaceutical from the first buffer tube.

19. A pharmaceutical order filling system comprising:
an automated dispensing device cooperatively comprising
a filling cabinet including a plurality of cells, each cell of the plurality of cells containing a quantity of a pharmaceutical selected from a plurality of pharmaceuticals,
a prefill assembly including a plurality of buffer tubes, each buffer tube of the plurality of buffer tubes being in respective communication with a particular cell of the plurality of cells, and a pallet assembly including an x-y movement apparatus adapted to engage and move a pallet within the pallet assembly, wherein a plurality of containers are disposed on the pallet, wherein the automated dispensing device is configured to dispense a first measured quantity of a first pharmaceutical from a first cell into a first holding area of a first buffer tube uniquely associated with the first cell and to dispense the first measured quantity of the first pharmaceutical from the first holding area of the first buffer tube into a first container when the first container is positioned below the first buffer tube, wherein the first pharmaceutical is among the plurality of pharmaceuticals, the first cell is among the plurality of cells, the first buffer tube is among the plurality of buffer tubes, and the first container is among the plurality of containers, wherein the first buffer tube comprises a buffer tube gate configured to release the first measured quantity of the first pharmaceutical from the first holding area, wherein the buffer tube gate is configured to flutter by opening and closing in quick succession, wherein the first cell comprises a funnel, wherein the first cell is adapted to receive an insert comprising a dispensing tube, and wherein the dispensing tube is adapted to engage and push open a funnel gate of the funnel when the insert is in the cell.

20. The system of claim 19 wherein the first buffer tube further comprises a second holding area and wherein the automated dispensing device is further configured to release the first measured quantity of the first pharmaceutical into the second holding area and to dispense a second measured quantity of the first pharmaceutical into the first holding area of the first buffer tube after the first measured quantity of the first pharmaceutical has been released into the second holding area.

21. The system of claim 19 wherein each of the plurality of buffer tubes is shaped as a long-draw funnel.

22. The system of claim 19 wherein the insert comprises a hopper, a vibratory bowl, and a level sensor, wherein the level sensor is configured to cause the hopper to spin and to release a released quantity of the first pharmaceutical into the vibratory bowl 906, wherein the released quantity of the first pharmaceutical comprises at least a portion of the first measured quantity of the first pharmaceutical.

23. The system of claim 19 wherein the pallet assembly comprises a lift apparatus configured to the pallet and lift the pallet such that the first container is aligned to receive the first measured quantity of the first pharmaceutical from the first buffer tube.

* * * * *